(12) United States Patent
Pullagurla et al.

(10) Patent No.: US 10,435,419 B2
(45) Date of Patent: Oct. 8, 2019

(54) PROCESS FOR THE PREPARATION OF TAVABOROLE, ITS NOVEL POLYMORPHIC FORMS AND THE POLYMORPHS THEREOF

(71) Applicant: Biophore India Pharmaceuticals PVT. Ltd., Hyderabad (IN)

(72) Inventors: Manik Reddy Pullagurla, Hyderabad (IN); Mecheril Valsan Nanda Kumar, Hyderabad (IN); Bhaskar Reddy Pitta, Hyderabad (IN); Jagadeesh Babu Rangisetty, Hyderabad (IN)

(73) Assignee: Biophore India Pharmaceuticals PVT. Ltd., Balanagar, Hyderabad (IN)

( * ) Notice: Subject to any disclaimer, the term of this patent is extended or adjusted under 35 U.S.C. 154(b) by 0 days.

(21) Appl. No.: 16/094,470

(22) PCT Filed: Jul. 21, 2016

(86) PCT No.: PCT/IN2016/050246
§ 371 (c)(1),
(2) Date: Oct. 18, 2018

(87) PCT Pub. No.: WO2017/183043
PCT Pub. Date: Oct. 26, 2017

(65) Prior Publication Data
US 2019/0119306 A1     Apr. 25, 2019

(30) Foreign Application Priority Data
Apr. 18, 2016 (IN) .............................. 201641013423

(51) Int. Cl.
*C07F 5/02* (2006.01)
*B01D 9/00* (2006.01)
*C07B 51/00* (2006.01)

(52) U.S. Cl.
CPC ............ *C07F 5/025* (2013.01); *B01D 9/0054* (2013.01); *C07B 51/00* (2013.01); *C07B 2200/13* (2013.01)

(58) Field of Classification Search
CPC ....................................................... C07F 5/025
See application file for complete search history.

(56) References Cited

U.S. PATENT DOCUMENTS 8,115,026 B2 *   2/2012   Baker ..................... C07F 5/025
                                                    558/288

FOREIGN PATENT DOCUMENTS

WO     WO2007078340 A2     7/2007

* cited by examiner

*Primary Examiner* — Golam M Shameem
(74) *Attorney, Agent, or Firm* — Ling Wu; Stephen Yang; Ling and Yang Intellectual Property

(57) ABSTRACT

The invention relates to novel process for preparation of Tavaborole. The invention also relates to novel polymorphic forms of Tavaborole and process for preparation of those polymorphic forms. The invention also relates to process for purification of Tavaborole to obtain the Tavaborole in significantly high yield and substantially pure form.

15 Claims, 3 Drawing Sheets

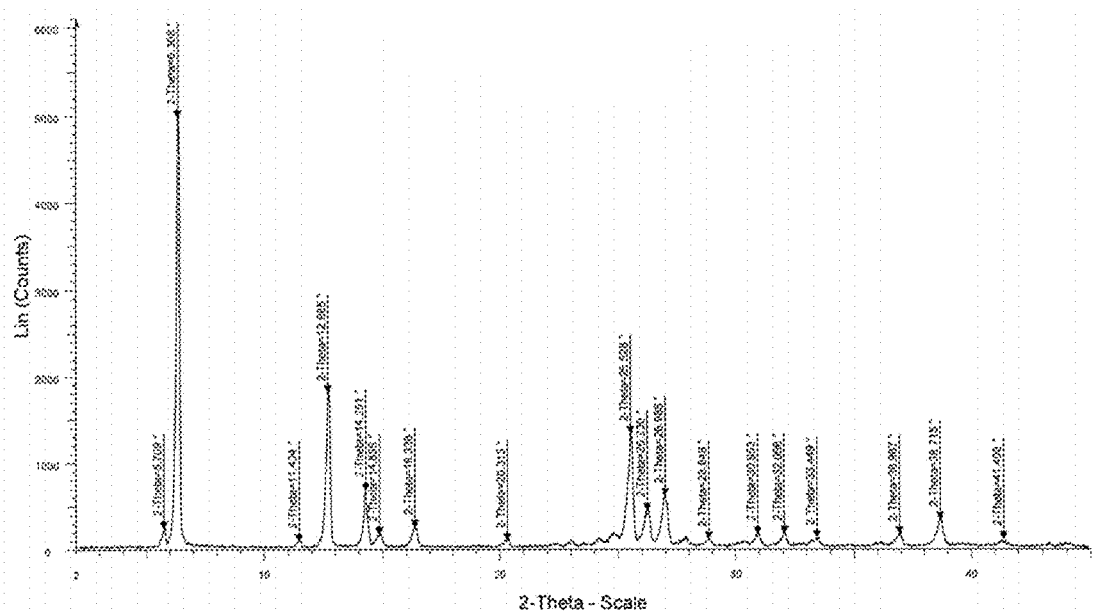
Figure-1: X-Ray powder diffraction pattern of Tavaborole Form I
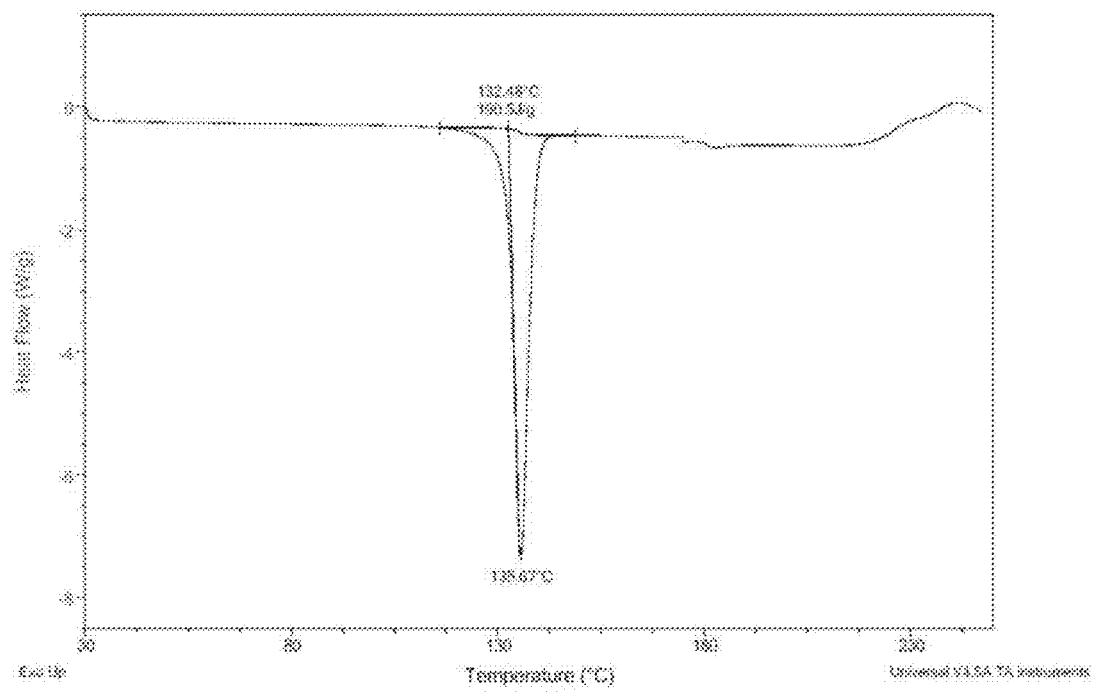
Figure-2: Differential Scanning Calorimetry (DSC) of Tavaborole of Form I

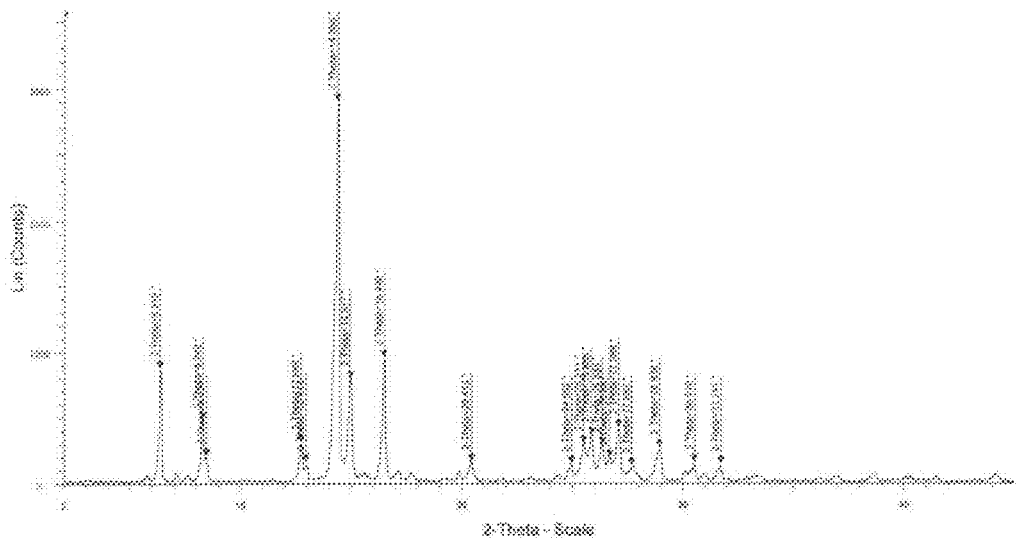
Figure-3: X-Ray powder diffraction pattern of Tavaborole Form II
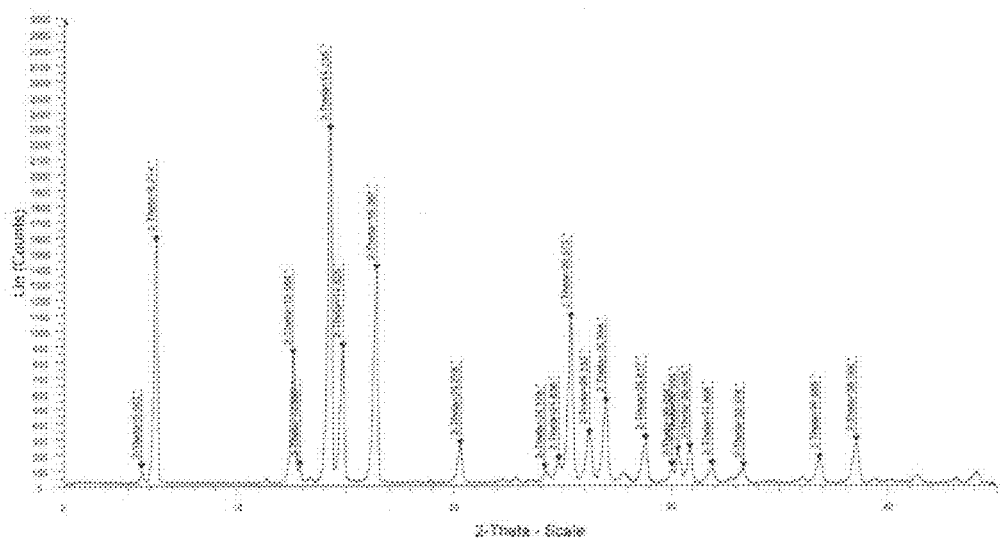
Figure-4: X-Ray powder diffraction pattern of Tavaborole Form III

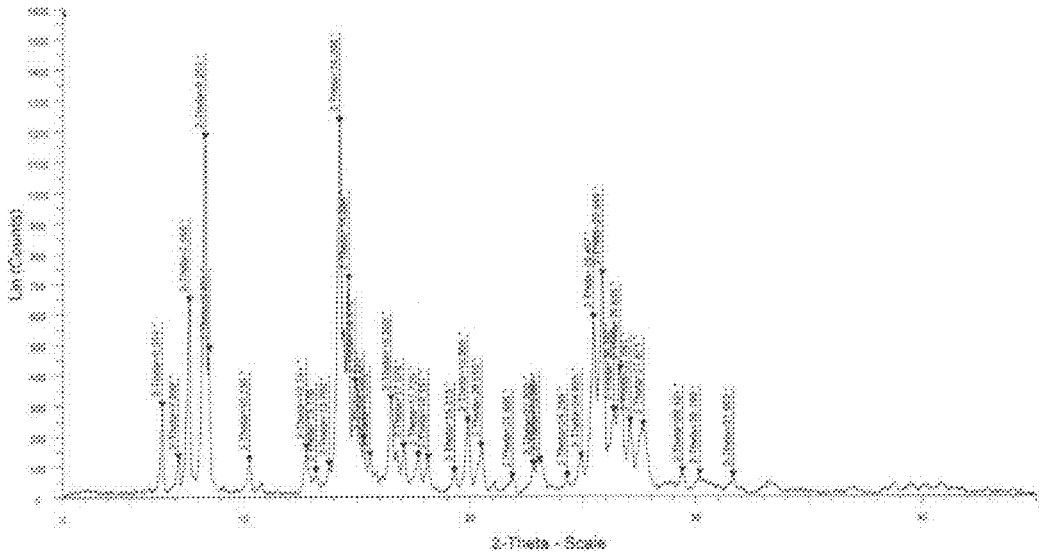
Figure-5: X-Ray powder diffraction pattern of Tavaborole Form IV
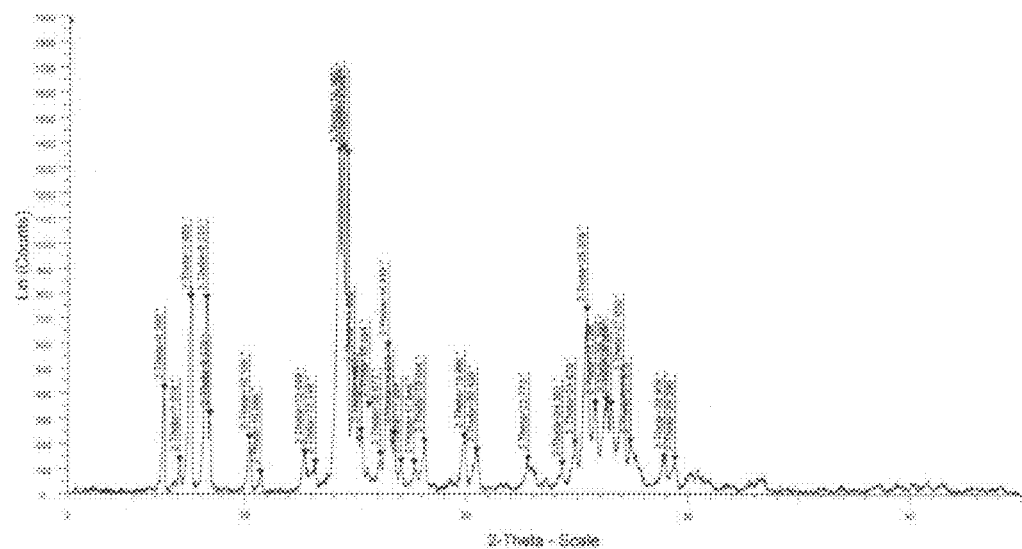
Figure-6: X-Ray powder diffraction pattern of Tavaborole Form V

PROCESS FOR THE PREPARATION OF TAVABOROLE, ITS NOVEL POLYMORPHIC FORMS AND THE POLYMORPHS THEREOF

FIELD OF THE INVENTION

The invention relates to novel process for preparation of Tavaborole. The invention also relates to novel polymorphic forms of Tavaborole and process for preparation of those polymorphic forms. The invention also relates to process for purification of Tavaborole to obtain the Tavaborole in significantly high yield and substantially pure form.

BACKGROUND OF THE INVENTION

The compound 5-fluoro-1,3-dihydro-1-hydroxy-2,1-benzoxaborole (Tavaborole) is represented by the formula 1:

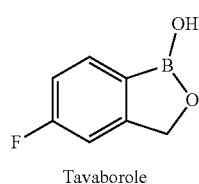

Tavaborole

Tavaborole is an oxaborole antifungal indicated for the topical treatment of onychomycosis of the toenails due to *Trichophyton rubrum* or *Trichophyton mentagrophytes*.

U.S. Pat. Nos. 5,880,188, 7,271,264, 8,115,026 reported various processes for the synthesis of oxaborole—specifically, Tavaborole, the contents of which are hereby incorporated as reference in their entirety.

General synthesis of Tavaborole is first described in the U.S. Pat. No. 5,880,188 (Prior art process-1). In this process oxaborole is made by converting an ortho-toluidine under Sandmeyer conditions to an O-substituted halogeno toluene which is then reacted with magnesium or alkyl lithium and the Grignard reagent or aryl lithium so formed is reacted with a borate ester to obtain a toluene boronic acid. This boronic acid is then reacted with NBS in CCl₄ solvent to give bromomethylbenzene boronic acid which is hydrolysed in alkali to give the benzaxoborole under acidic conditions.

Prior Art Process-1

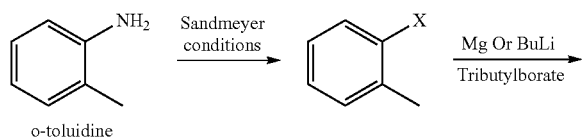

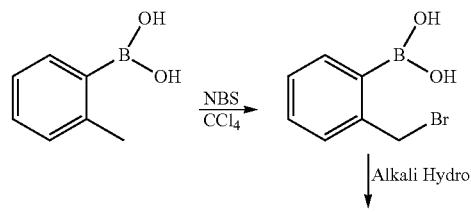

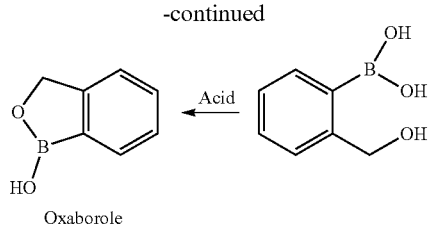

Oxaborole

In this process, the reported yield of the bromination stage is ~15% and the overall yield is less than 5%, which makes the process impractical at a commercial scale production.

Another route for the preparation of oxaborole derivatives reported in the U.S. Pat. No. 5,880,188 (Prior art process-2) includes reacting benzaldehyde with p-toluenesulphonylhydrazide and reacting the product obtained subsequently with boron tribromide in the presence of a ferric or aluminium chloride which give the cyclized tosyl compound. The Tosyl compound on subsequent alkaline hydrolysis generates oxaborole compound.

Prior Art Process-2

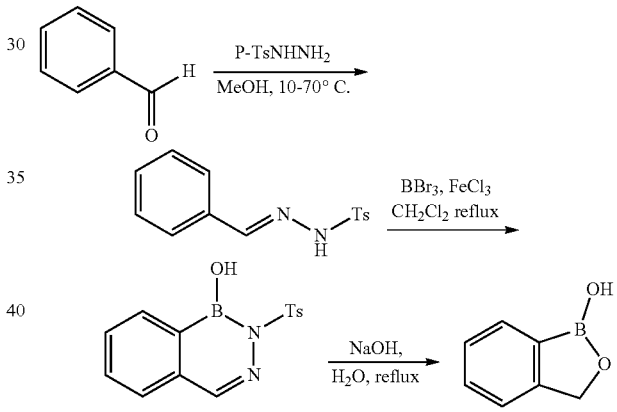

In this process, the reported yield of tosylhydrazone to oxaborole conversion is less than 10%.

U.S. Pat. No. 7,271,264 presents another route of synthesis for Tavaborole (Prior art process-3). In this process, (2-bromo-5-fluoro-phenyl)-methanol is treated with ethyl-vinyl ether in presence of PPTS to give 1-bromo-2-(1-ethoxy-ethoxymethyl)-4-fluoro-benzene, which on further treatment with n-BuLi followed by reaction with trimethyl borate, and later with 1N HCl generates Tavaborole.

Prior Art Process-3

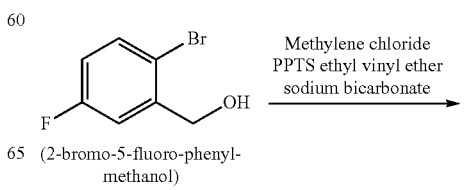

(2-bromo-5-fluoro-phenyl-methanol)

3

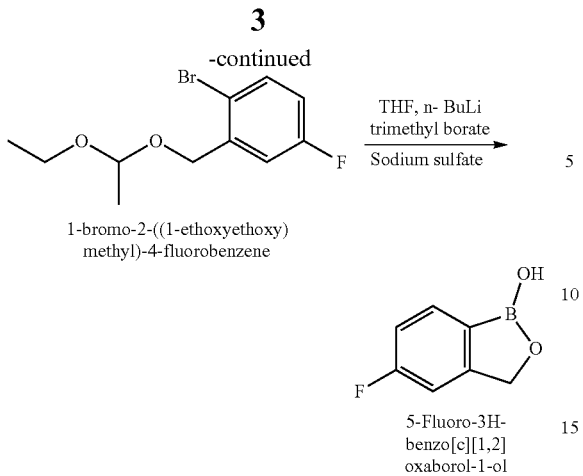

1-bromo-2-((1-ethoxyethoxy)
methyl)-4-fluorobenzene

5-Fluoro-3H-
benzo[c][1,2]
oxaborol-1-ol

This process involves highly pyrophoric Butyllithium making it unsuitable for industrial scale synthesis.

U.S. Pat. No. 8,115,026 patent also describes a general route for the preparation of oxaborole compound including Tavaborole (Prior art process-4). In this process, orthohalo carbonyl compound is treated with bispinacolato diboran or pinacol borane in the presence of Pd catalyst, ligand and a base to give Pinacol borate which on oxidative cleavage with NaIO$_4$ generates boronic acid compound. Reduction of the carbonyl group of boronic acid compound with a suitable reducing agent produces the crude oxaborole compound and that is purified by column chromatography.

Prior Art Process-4

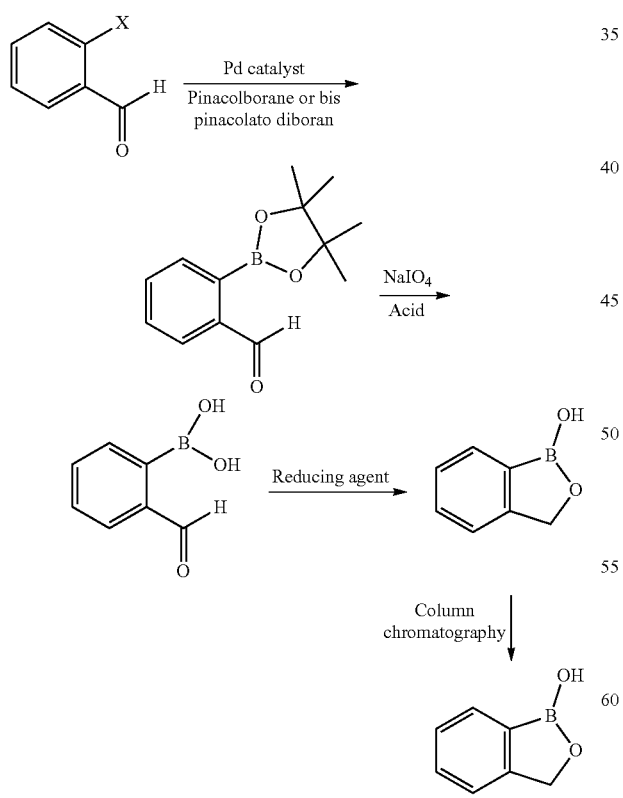

Even though the process avoids pyrophoric Butyllithium, it requires 30 mole percentage of expensive Palladium catalyst. In addition, this process involves column chromatographic purification of final compound and the overall yield is ~21%.

Therefore, there is a need in the art for a new or improved method for the preparation of Tavaborole in significantly high yield compared to the prior art. In view of this, the present inventors provide a safe, cost-effective and industrially applicable process for the preparation of Tavaborole in significantly high yield.

OBJECTS OF THE INVENTION

Primary object of the invention is to provide novel process for the preparation of Tavaborole.

Another object of the invention is to provide novel polymorphic forms of Tavaborole.

Another object of the invention is to provide process for preparation of the novel polymorphic forms of Tavaborole.

Another object of the invention is to provide process for preparation of Tavaborole with high yield and purity.

Another object of the invention is to provide process for purification of Tavaborole to obtain highly purified Tavaborole.

A further object of the invention is to provide Tavaborole without the impurities represented as Impurity A and Impurity B.

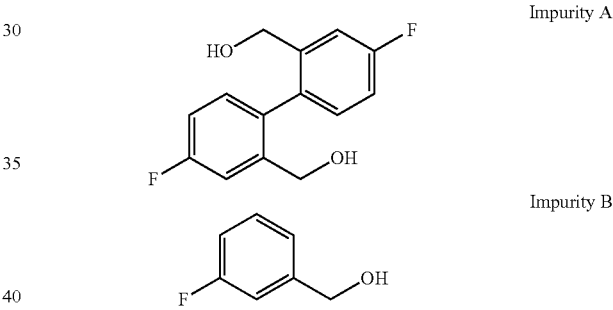

Impurity A

Impurity B

SUMMARY OF THE INVENTION

Accordingly, the present invention provides novel synthetic methods for the preparation of 5-fluoro-1,3-dihydro-1-hydroxy-2,1-benzoxaborole (Tavaborole 1).

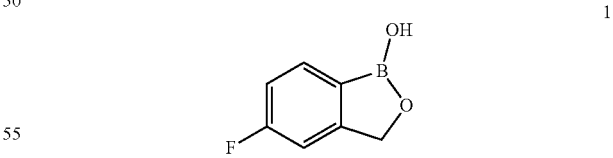

1

In one aspect of the invention, synthesis of Tavaborole is reported which result in significantly high yield, greater than 80%.

In one aspect of the invention methods of purification of Tavaborole to obtain a substantially pure compound, whose purity is greater than or equal to 99% is reported.

In another aspect of the invention, Tavaborole obtained by the reported purification procedures of the invention has purity greater than or equal to 99% and is devoid of the major reaction impurities (A&B).

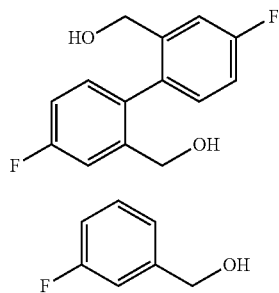

Impurity A

Impurity B

One of the processes for the preparation of Tavaborole according to the invention comprises three steps as depicted in Scheme-1.

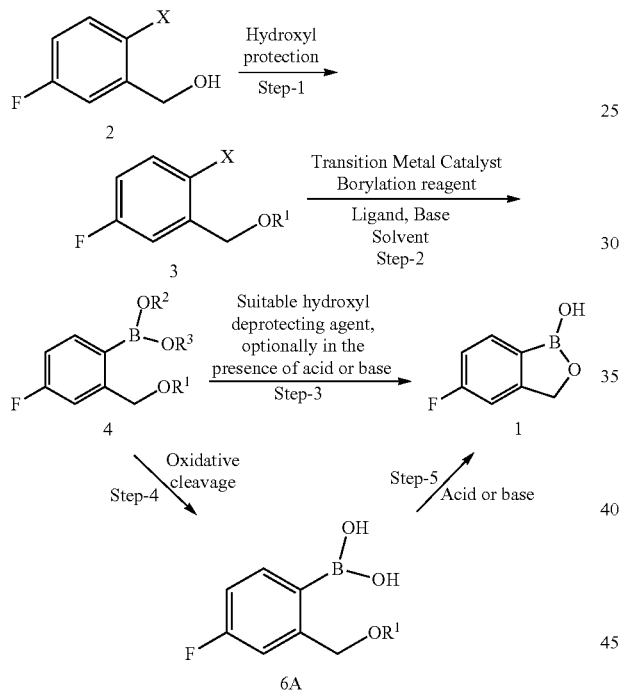

Wherein
X is a member selected from Br, I, OTf;
$R^1$ is hydroxyl protecting group; and
$R^2$, $R^3$ are members independently selected from H; substituted or unsubstituted $C_1$-$C_8$ alkyl; substituted or unsubstituted heteroalkyl $C_1$-$C_8$; substituted or unsubstituted aryl $C_5$-$C_{10}$; substituted or unsubstituted heteroaryl $C_5$-$C_{10}$; substituted or unsubstituted cycloalkyl $C_3$-$C_8$; substituted or unsubstituted heterocycloalkyl $C_3$-$C_8$; together with the atoms to which they are attached may be optionally joined to form a 4- to 8-membered ring.

i. The first step of the synthetic Scheme-1 comprises protecting the primary hydroxyl moiety of the compound 2 with a suitable hydroxyl protecting agent to generate compound 3.
ii. The second step comprises conversion of hydroxyl protected compound 3 into a borate compound 4 (an ester or an acid—when $R^2$, $R^3$='H') via a transition metal catalyzed cross-coupling reaction.
iii. The third and the final step involves conversion of borate compound 4 into Tavaborole (1)
   a) either by simultaneous deprotection of hydroxyl protecting group and borate group (ester or acid, when $R^2$, $R^3$='H') using a suitable deprotecting agent optionally in the presence of an acid or a base; or
   b) by sequential deprotection of hydroxyl protecting group and boronate ester group under suitable conditions followed by dehydrative cyclization in the presence of suitable acid or a base.

Compound 4 can be converted to Tavaborole by an alternate route via formation of 6A. The reaction stage includes oxidative cleavage of compound 4 by treating with $NaIO_4$ or $Pb(OAc)_4$ in a suitable solvent followed by cyclization in the presence of an acid or a base.

In another embodiment of the invention Tavaborole is synthesized by the reaction depicted in Scheme-2.

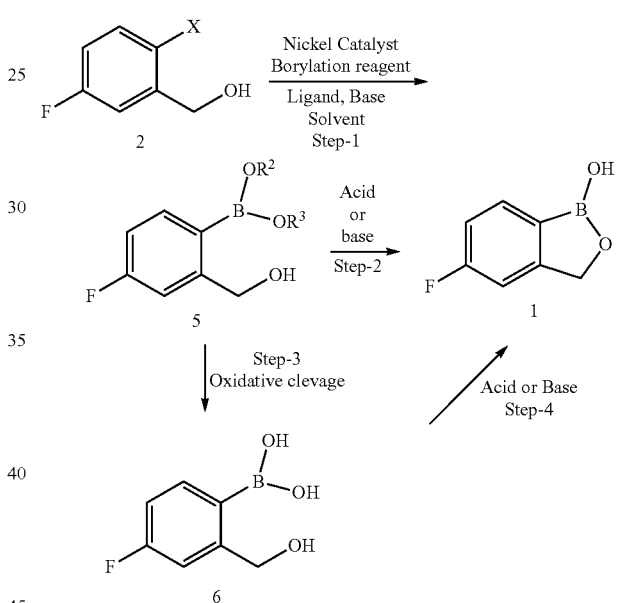

wherein the substituents X, $R^2$, $R^3$ are as defined above.
i. The first step of the process of Scheme-2 comprises, conversion of the fluoro-phenyl compound 2 into borate compound 5 (ester or acid—when $R^2$, $R^3$='H') via a Nickel catalyzed cross-coupling reaction. In this process, the reaction is performed in the absence of any protection to primary hydroxyl moiety of compound 2.
ii. Step-2 comprises conversion of borate compound 5 into Tavaborole (1) under acid or base mediated hydrolysis conditions.
iii. Step-3, alternatively comprises oxidative cleavage of the borate compound 5 to generate compound 6 and subsequent dehydrative cyclization into Tavaborole (1) in the presence of an acid or a base.

In yet another aspect of the invention, crystalline polymorphic Forms I, II, III, IV & V of Tavaborole and processes for their preparation are reported.

In one embodiment the invention provides a process for preparation of 5-fluoro-1,3-dihydro-1-hydroxy-2,1-benzoxaborole (Tavaborole) comprising the steps of:

(i) protecting primary hydroxyl moiety of compound 2 with a hydroxyl protecting agent to obtain hydroxyl protected compound 3;
(ii) converting the hydroxyl protected compound 3 into a borate compound 4 using a borylation reagent via a transition metal catalyzed cross-coupling reaction; and
(iii) converting the borate compound 4 into Tavaborole;
wherein the compounds 2, 3 and 4 and their substituents are as described above for Scheme-1.

The borate compound 4 in step (iii) is converted into Tavaborole either by simultaneous deprotection of hydroxyl protecting group and boronate ester group using a hydroxyl deprotecting agent, or by sequential deprotection of hydroxyl protecting group and boronate ester group of compound 4 followed by cyclization in presence of an acid or a base.

The hydroxyl protecting agent comprises acyl protecting agent selected from the group consisting of acetyl chloride, acetic anhydride, and benzoyl chloride or Silyl protecting agents selected from the group consisting of trimethyl silyl chloride, triethyl silyl chloride, and tertiary butyl dimethyl silyl chloride (TBDMSCl).

The transition metal catalyzed cross-coupling reaction of step (ii) is carried out in presence of Pd catalyst selected from PdCl$_2$(dppf), [PdCl$_2$dppf]CH$_2$Cl$_2$, PdCl$_2$(PPh$_3$)$_2$, Pd(PPh$_3$)$_4$, Pd(OAc)$_2$, [Pd$_2$dba$_3$], [Pd(allyl)Cl]$_2$, Pd(acac)$_2$, PhPd(OAc)(PPh)$_2$ or any Palladium catalyst that generates in situ Pd(O) and combinations thereof or Ni catalyst selected from NiCl$_2$(dppp), NiCl$_2$(dppf), NiCl$_2$(dppe), NiCl$_2$.glyme, NiBr$_2$.glyme, NiCl$_2$(PPh$_3$)$_2$, NiCl$_2$(PCy$_3$)$_2$, Ni(PPh$_3$)$_4$, Ni(PPh$_3$)$_4$, Ni(COD)$_2$, NiCl$_2$, NiBr$_2$ or any Nickel catalyst that generates in situ Ni(O) and combinations thereof.

The borylation reagent is selected from the group consisting of Bis(neopentylglycolato)diboron, Bis(catecholato) diboron, Bis(hexyleneglycolato)diboron, Bis(pinacolato)diboron, Tetrahydroxydiboron, Pinacolborane, Methylpentanediolborane, Catecholborane, Neopentylglycoborane and Trialkyl borate.

The reaction of step (ii) is carried out in presence of a solvent selected from toluene, xylene, N,N-dimethylformamide, dimethylsufoxide, tetrahydrofuran and 1,4-dioxane or mixtures thereof.

The reaction of step (ii) is carried out in presence of a ligand selected from the group consisting of Xphos, MeO-CM-Phos, Sphos, DavePhos, RuPhos, tBu$_3$P—HBF$_4$, QPhos, JohnPhos, Me$_4$-tBu-XPhos, Ad$_2$PBu, BrettPhos, AmPhos, PPh$_3$ and tri(o-tolyl)phosphine.

The transition metal catalyst in step (ii) further comprises co-catalyst selected from the group consisting of Cu(OTf)$_2$, Cu(OAc)$_2$, CuCl, CuBr, CuI, ZnCl$_2$ and Ag$_2$CO$_3$.

The deprotection of hydroxyl protecting group is carried out by a hydroxyl deprotecting agent comprising an inorganic base selected from potassium hydroxide, lithium hydroxide and sodium hydroxide, metal carbonates selected from potassium carbonate, sodium carbonate and cesium carbonate, metal alkoxides selected from sodium methoxide and sodium ethoxide.

The deprotection of hydroxyl protecting group is carried out by a hydroxyl deprotecting agent comprising an acid deprotecting agent selected from HCl, H$_2$SO$_4$, HNO$_3$, AcOH, HCOOH, BF$_3$Et$_2$O, AlCl$_3$ and BBr$_3$.

The cyclization is carried out using an acid selected from the group consisting of HCl, H$_2$SO$_4$, HNO$_3$, AcOH, HCOOH, BF$_3$Et$_2$O, AlCl$_3$ and BBr$_3$.

In another embodiment, the invention provides a process for preparation of Tavaborole comprises the steps of:

(i) protecting primary hydroxyl moiety of a compound of 2a with acetic anhydride in presence of DCM and pyridine to obtain hydroxyl protected compound 3a;

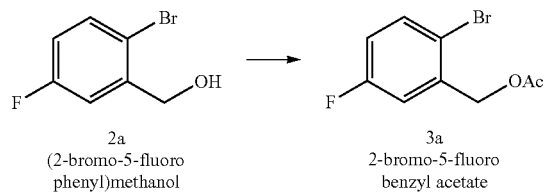 [SMILES: OCc1cc(F)ccc1Br ; CC(=O)OCc1cc(F)ccc1Br]

2a
(2-bromo-5-fluoro phenyl)methanol 3a
2-bromo-5-fluoro benzyl acetate (ii) converting the hydroxyl protected compound 3a obtained in step (i) into a borate compound 4a using bis(pinacolato)diboron via PdCl$_2$(dppf) catalyzed cross-coupling reaction in presence of 1,4-dioxane and potassium acetate (KOAc), wherein the reaction is carried out at temperature between 70° C. to 120° C.;

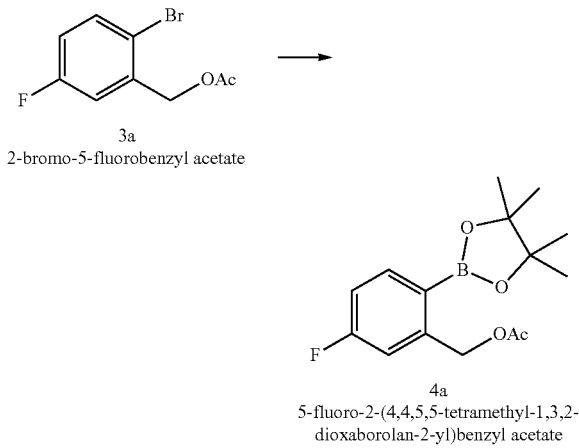

3a
2-bromo-5-fluorobenzyl acetate 4a
5-fluoro-2-(4,4,5,5-tetramethyl-1,3,2-dioxaborolan-2-yl)benzyl acetate (iii) simultaneous deprotection of hydroxyl protecting group and boronate ester group of borate compound 4a obtained in step (ii) by treatment with acid HCl or base NaOH to obtain Tavaborole.

In another embodiment, the invention provides a process for preparation of Tavaborole comprising following steps:

(i) protecting primary hydroxyl moiety of a compound 2b with TBDMSCl in presence of dichloromethane (DCM) and imidazole to obtain hydroxyl protected compound 3b;

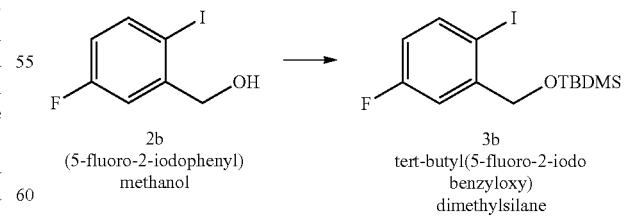

2b
(5-fluoro-2-iodophenyl) methanol 3b
tert-butyl(5-fluoro-2-iodo benzyloxy) dimethylsilane (ii) converting the hydroxyl protected compound 3b obtained in step (i) into a borate compound 4b using bis(pinacolato)diboron via Pd(OAc)$_2$ catalyzed cross-coupling reaction in presence of acetonitrile, Tri-O-tolylphosphine, Cs$_2$CO$_3$ and CuI;

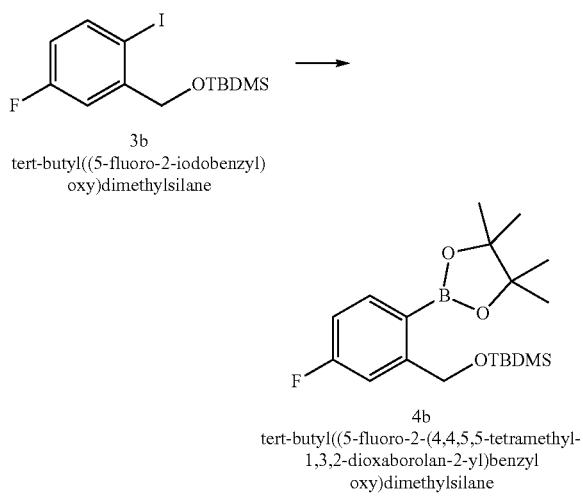

3b
tert-butyl((5-fluoro-2-iodobenzyl)oxy)dimethylsilane 4b
tert-butyl((5-fluoro-2-(4,4,5,5-tetramethyl-1,3,2-dioxaborolan-2-yl)benzyl oxy)dimethylsilane (iii) treating compound 4b obtained in step (ii) with sodium periodate (NaIO₄Cl presence of acetone, water and ammonium acetate followed by further treatment with HCl to obtain Tavaborole.

In another embodiment, the invention provides a process for preparation of 5-fluoro-1,3-dihydro-1-hydroxy-2,1-benzoxaborole (Tavaborole) comprising the steps of:
(i) converting a compound 2 into a borate ester compound 5 using a borylation reagent via a transition metal catalyzed cross-coupling reaction;
(ii) converting the borate ester compound of formula 5 obtained in step (i) into Tavaborole;

The conversion of borate ester compound 5 into Tavaborole in step (ii) comprises the sub-steps of:
(i) oxidative cleaving of the borate ester compound of formula 5 into a compound of formula 6;
(ii) converting the compound of formula 6 into Tavaborole in presence of an acid.

The above said compounds 2, 5 and 6 and their substituents are as described above for Scheme-2.

The transition metal catalyzed cross-coupling reaction of step (i) is carried out in presence of Pd catalyst selected from PdCl₂(dppf), [PdCl₂dppf]CH₂Cl₂, PdCl₂(PPh₃)₂, Pd(PPh₃)₄, Pd(OAc)₂, [Pd₂dba₃], [Pd(allyl)Cl]₂, Pd(acac)₂, PhPd(OAc)(PPh)₂ or any Palladium catalyst that generates in situ Pd(O) and combinations thereof; or Ni catalyst selected from NiCl₂(dppp), NiCl₂(dppf), NiCl₂(dppe), NiCl₂.glyme, NiBr₂.glyme, NiCl₂(PPh₃)₂, NiCl₂(PCy₃)₂, Ni(PPh₃)₄, Ni(PPh₃)₄, Ni(COD)₂, NiCl₂, NiBr₂ or any Nickel catalyst that generates in situ Ni(O) and combinations thereof.

The borylation reagent is selected from the group consisting of Bis(neopentylglycolato)diboron, Bis(catecholato)diboron, Bis(hexyleneglycolato)diboron, Bis(pinacolato)diboron, Tetrahydroxydiboron, Pinacolborane, Methylpentanediolborane, Catecholborane, Neopentylglycoborane and Trialkyl borate.

The reaction of step (i) is carried out in a solvent selected from MeOH, EtOH, IPA, toluene, xylene, N,N-dimethylformamide, dimethylsufoxide, tetrahydrofuran and 1,4-dioxane or mixtures thereof.

The reaction of step (i) is carried out in presence of a base comprising an inorganic base selected from the group consisting of KOPh, KOAc, NaOAc, NH₄OAc, Cu(OAc)₂, Cs₂CO₃, K₂CO₃, Na₂CO₃, Ag₂CO₃, K₃PO₄, NaOH, KOH, CsOH, KOMe, NaOMe, LiOtBu, NaOtBu and KOtBu or an organic base selected from the group consisting of pyridine, triethyl amine, leutidine, DABCO, DBU, 1,2,2,6,6-pentamethylpipiridine, 1,1,3,3-tetramethylguanidine, iPr₂NEt, NBu₃ and Cy₂NMe.

The reaction of step (i) is carried out in presence of a ligand selected from the group consisting of Xphos, MeO-CM-Phos, Sphos, DavePhos, RuPhos, tBu₃P—HBF₄, QPhos, JohnPhos, Me₄-tBu-XPhos, Ad₂PBu, BrettPhos, AmPhos, PPh₃ and tri(o-tolyl)phosphine.

The transition metal catalyst in step (i) further comprises co-catalyst selected from the group consisting of Cu(OTf)₂, Cu(OAc)₂, CuCl, CuBr, CuI, ZnCl₂ and Ag₂CO₃.

The oxidative cleaving in step (i) comprises treating the compound of formula 5 with NaIO₄ or Pb(OAc)₄ in presence of a solvent selected from the group consisting of H₂O, tetrahydrofuran, 1,4-dioxane, methanol and ethanol or mixtures thereof.

The acid in step (ii) is selected from the group consisting of HCl, H₂SO₄, AcOH, HCOOH, BF₃Et₂O, AlCl₃ and BBr₃.

The above said processes further comprises purification of the Tavaborole with solvents comprising alkanes consisting of Hexanes, Toluene and cyclohexane, alcohols consisting of Methanol, Ethanol and Isopropyl alcohol, water, Acetonitrile, Tetrahydrofuran, Acetone, Ethyl acetate, and Dichloromethane or mixtures thereof.

In one embodiment, the invention provides a process for purification of Tavaborole comprising the steps selected from:
(a) mixing Tavaborole in a solvent and treating the solution with an anti solvent;
(b) mixing Tavaborole in a solvent, optionally heating the solution to dissolve the compound and isolating the pure compound by cooling the solution;
(c) treating Tavaborole with silica gel in a solvent followed by recrystallization; and
(d) dissolving Tavaborole in aqueous alkali solution followed by washing with Ethyl acetate, adjusting the pH of the aqueous layer to acidic with HCl, and filtering the precipitated solid;
wherein the solvent in any of the above process is selected from alkanes consisting of Hexanes, Toluene and cyclohexane, alcohols consisting of Methanol, Ethanol and Isopropyl alcohol, water, Acetonitrile, Tetrahydrofuran, Acetone, Ethyl acetate, and Dichloromethane or mixtures thereof; and wherein the anti-solvent is water.

In another embodiment, the invention provides process for purification of Tavaborole comprising the steps selected from:
(a) dissolving crude Tavaborole in Acetonitrile at 25-60° C. and isolating by adding anti-solvent water to obtain the pure product;
(b) dissolving crude Tavaborole in a mixture of IPA and toluene at 40-80° C. and isolating by cooling the solution to obtain the pure product;
(c) treating crude Tavaborole with silica gel in toluene and recrystallizing in hexane to obtain the pure product; and
(d) dissolving crude Tavaborole in a mixture solution of Tolune and acetonitrile at higher temperature, gradually cooling the mass to precipitate the solid, filtering the obtained solid and drying to obtain the pure product.

In another embodiment, the invention provides process for purification of Tavaborole to obtain purified Tavaborole with more than 99% purity comprising the steps of:
(a) dissolving crude Tavaborole in a solvent at 50-80° C.;
(b) cooling the solution to 0-5° C.; and
(c) filtering and drying to obtain purified Tavaborole with a purity more than or equal to 99%;

wherein the solvent in step (a) is selected from a mixture of IPA/ethyl acetate (3:4), a mixture of Toluene/IPA (5:1), a mixture of Toluene/Acetonitrile (4:2), a mixture of ethanol/water (1:5); and a mixture of Acetonitrile/water (1:10).

wherein the purified Tavaborole obtained by the process has more than 99% purity and does not contain process impurities represented as Impurity-A and Impurity-B.

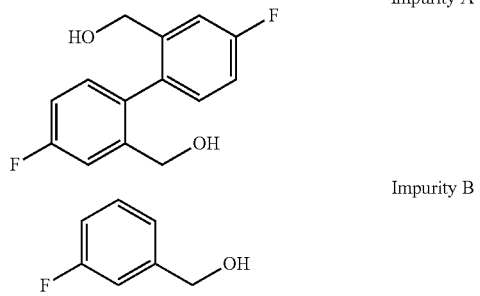

Impurity A

Impurity B

In another aspect, the invention provides purified 5-fluoro-1,3-dihydro-1-hydroxy-2,1-benzoxaborole (Tavaborole 1) with greater than 99% purity and without the impurities represented as Impurity-A and Impurity-B.

In another aspect, the invention provides a process for preparation of crystalline forms of Tavaborole comprising the steps of:
(a) contacting Tavaborole with a solvent or mixture of solvents;
(b) heating the solvent or solvents mixture with Tavaborole to reflux; and
(c) precipitating Tavaborole from solvent or solvents mixture by using conventional techniques viz. slow or fast cooling, addition of crystallization solvent, drying at atmospheric or reduced pressure, so as to obtain the desired crystalline form of Tavaborole;
wherein the solvent or solvents mixture can be selected from water, methanol, Ethanol, Isopropyl alcohol, Methyl tertiary butyl alcohol, Toluene, acetone Tetrahydrofuran, Ethyl acetate, dichloromethane, acetonitrile, methyl tertiary butyl ether or mixtures thereof; and
wherein the crystalline forms of Tavaborole produced by the process is any of polymorphic forms Form-I, Form-II, Form-III, Form-IV and Form-V, each polymorphic form is characterized by XRPD peaks patterns as depicted in FIG. 1, FIG. 3, FIG. 4, FIG. 5 and FIG. 6 respectively.

The invention further provides:
Crystalline Form I of Tavaborole, characterized by X-ray powder diffraction (XRPD) pattern comprising one or more of the reflections at value 6.30, 12.66 and 25.5±0.2 degrees 2 theta (2θ°) and which has X-ray powder diffraction pattern as shown in FIG. 1; and further characterized by XRPD pattern comprising one or more of the reflections at value: 5.70, 11.43, 14.25, 14.83, 16.33, 20.31, 26.23, 26.98, 28.84, 30.95, 32.06, 33.44, 36.96, 38.71, 41.40±0.2 degrees 2 theta (2θ°).

A process for preparing crystalline Form I of Tavaborole comprising refluxing Tavaborole in a mixture of acetonitrile and toluene and isolating Tavaborole by cooling to 0-5° C.

Crystalline Form II of Tavaborole characterized by X-ray powder diffraction (XRPD) pattern comprising one or more of the reflections at value 6.31, 14.35, 14.91, 16.44 and 27.08±0.2 degrees 2 theta (2θ°) and which has X-ray powder diffraction pattern as shown in FIG. 3; and further characterized by XRPD pattern comprising one or more of the reflections at value: 12.68, 12.91, 20.41, 24.95, 25.51, 25.85, 26.33, 26.68, 27.08, 27.68, 28.93, 30.51, 31.74±0.2 degrees 2 theta (2θ°).

Crystalline Form III of Tavaborole characterized by X-ray powder diffraction (XRPD) pattern comprising one or more of the reflections at value 6.21, 12.55, 14.23, 14.82, 16.36, 25.37, and 26.99±0.2 degrees 2 theta (2θ°) and which has X-ray powder diffraction pattern as shown in FIG. 4; and further characterized by XRPD pattern comprising one or more of the reflections at value 5.56, 12.88, 20.27, 24.17, 24.83, 25.37, 26.23, 26.99, 28.81, 30.05, 30.33, 30.9, 31.9, 33.37, 36.88 and 38.56±0.2 degrees 2 theta (2θ°).

Crystalline Form IV of Tavaborole, characterized by X-ray powder diffraction (XRPD) pattern comprising one or more of the reflections at value: 6.35, 7.55, 8.25, 8.46, 14.2, 14.6, 14.9, 16.5, 25.46, 25.84, 26.38 and 26.63±0.2 theta degree (2θ°) and which has X-ray powder diffraction pattern as shown in FIG. 5; and further characterized by XRPD pattern comprising one or more of the reflections at value 7.09, 10.23, 12.74, 13.17, 13.76, 15.27, 15.55, 17.07, 17.72, 18.15, 19.31, 19.90, 20.51, 21.88, 22.8, 23.08, 24.29, 24.92, 27.09, 27.67, 29.42, 30.19 and 31.66±0.2° 2θ.

Crystalline Form V of Tavaborole characterized by X-ray powder diffraction (XRPD) pattern comprising one or more of the reflections at 6.3, 7.48, 8.21, 8.37, 14.16, 14.35, 14.54, 14.88, 15.55, 16.41, 25.37, 25.78, 26.29, 26.5 and 27.03±0.2° 2θ and which has X-ray powder diffraction pattern as shown in FIG. 6; and further characterized by XRPD pattern comprising one or more of the reflections at value 7.01, 10.16, 10.68, 12.64, 13.14, 15.2, 16.07, 16.67, 17.05, 17.64, 18.08, 19.88, 20.43, 22.77, 24.3, 24.87, 26.29, 27.37, 28.90, 29.39±0.2° 2θ.

BRIEF DESCRIPTION OF DRAWINGS

FIG. 1: represents a characteristic X-Ray powder diffraction pattern of Tavaborole Form I FIG. 2: represents a characteristic differential scanning calorimetry (DSC) of Tavaborole of Form I FIG. 3: represents a characteristic X-Ray powder diffraction pattern of Tavaborole Form II FIG. 4: represents a characteristic X-Ray powder diffraction pattern of Tavaborole Form III FIG. 5: represents a characteristic X-Ray powder diffraction pattern of Tavaborole Form IV FIG. 6: represents a characteristic X-Ray powder diffraction pattern of Tavaborole Form V

DETAILED DESCRIPTION OF THE INVENTION

The present invention relates to processes for the preparation of Tavaborole in significantly high yield and substantially pure form. The invention also comprises novel polymorphic forms of Tavaborole and processes for their preparation. The invention also provides processes for purification of Tavaborole to obtain substantially pure Tavaborole, comprising purity more than or equal to 99% and devoid of process related impurities represented as Impurity A and Impurity B.

The methods for the preparation of Tavaborole are schematically represented by Scheme-1 and Scheme-2.

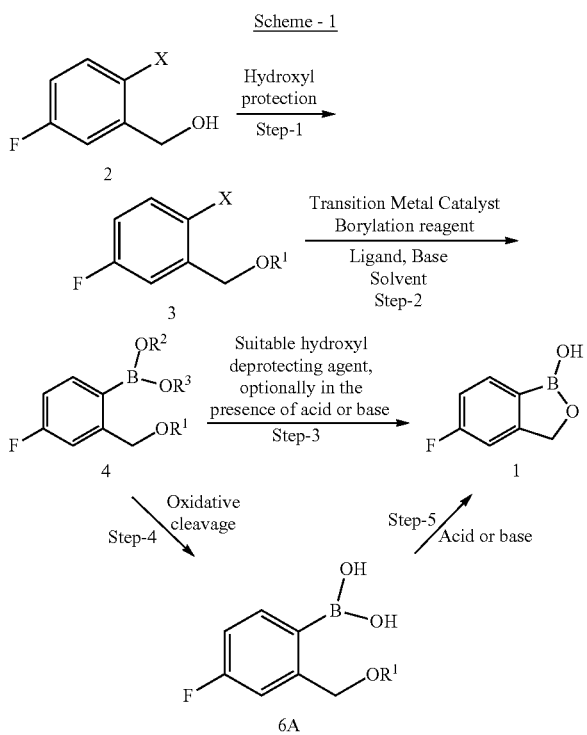

One of the reported procedures of the invention (Scheme-1), comprises
i. Conversion of compound 2 into compound 3 using a suitable hydroxyl protecting agent.
Non limiting examples of the suitable hydroxyl protecting groups/agents are as defined under "definitions". In one aspect of the invention, the hydroxyl protecting group is the acyl protecting agent preferably acetic anhydride and the reaction is carried out in dichloromethane as solvent at room temperature in the presence of catalytic amount of pyridine. In another aspect of the invention, the hydroxyl protecting group is the silyl protecting agent preferably TBDMSCl and the reaction is carried out in THF solvent in the presence of imidazole base.
ii. Conversion of compound 3 into borate compound 4 via a transition metal catalyzed cross-coupling reaction.
Non limiting examples of the borylation reagent, transition metal catalyst, ligands and the solvent employed are as defined hereunder. Compound 3 is treated with 1 to 2 equivalents of borylation reagent in the presence of 1 to 4 mol % (0.01 to 0.04 equivalents with respect to compound 3, transition metal catalyst, 1 to 5 equivalents of base and/or with the use of appropriate ligand in a suitable solvent. Occasionally these metal catalyst reactions may be conducted in the presence of additive or co-catalyst. Reaction temperatures range from 70° C. to 120° C., preferably 80° C. to 90° C. Reaction completion times range from 10 minutes to 24 hrs, preferably 6-8 hrs.
Suitable solvent used for this reaction step is selected from the group comprising toluene, xylene, N,N-dimethylformamide, dimethylsufoxide, tetrahydrofuran, 1,4-dioxane or mixtures thereof. In one aspect of the invention, the most preferred solvent used for the reaction is 1,4-dioxane.
iii. Conversion of compound 4 into Tavaborole (1)
a) either by simultaneous deprotection of hydroxyl protecting group and the borate group (ester or acid, when $R^2$, $R^3$='H') of compound 4 using a suitable deprotecting agent optionally in the presence of an acid or base; or
b) by sequential deprotection of hydroxyl protecting group and boronate ester group under suitable conditions followed by cyclization in the presence of an acid or a base, the most preferred acid is HCl and the most preferred base is NaOH.

Compound 4 can be converted to Tavaborole by an alternate route via the formation of 6A. The reaction stage includes oxidative cleavage of compound 4 by treating with 1 to 3 equivalents of $NaIO_4$ or $Pb(OAc)_4$ in a suitable solvent followed by dehydrative cyclization in the presence of an acid or a base. Suitable solvent is selected from the group comprising $H_2O$, tetrahydrofuran, 1,4-dioxane, methanol, ethanol or mixtures thereof. Another route of synthesis of Tavaborole is as represented in Scheme-2 below:

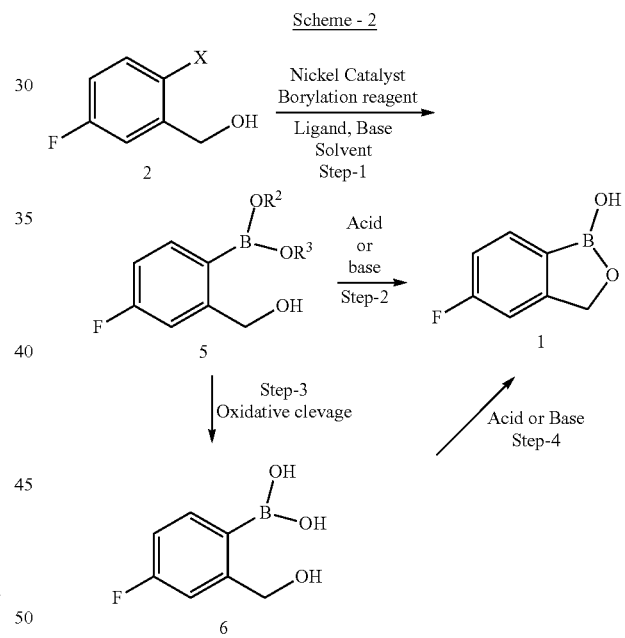

wherein the substituents X, $R^2$, $R^3$ are as defined above and the process comprises
i. Conversion of compound 2 into compound 5 via a Nickel catalyzed cross-coupling reaction.
Compound 2 is treated with 1 to 2 equivalents of borylation reagent in the presence of 5 to 15 mol % (0.05 to 0.15 equivalents with respect to compound 2) of Nickel catalyst, 2 to 5 equivalents of base in a suitable solvent, optionally with the use of appropriate ligand.
Reaction temperatures may range from 25° C. to 95° C., preferably 35° C. to 40° C. Reaction completion times range from 1 hr to 24 hr, preferably 10 to 12 hr.
Suitable solvent is selected from the group comprising methanol, ethanol, IPA, N,N-dimethylformamide, dimethylsufoxide, tetrahydrofuran, 1,4-dioxane or mixtures thereof.

The non limiting examples of the Nickel catalyst, base and the ligand is as described hereunder.

ii. In step-2, compound 5 is converted into Tavaborole (1) under acid or base mediated hydrolysis conditions.

The acid used for the hydrolysis is selected from the group comprising HCl, $H_2SO_4$, AcOH, HCOOH, $BF_3Et_2O$, $AlCl_3$, $BBr_3$ or the like and the base is selected from the group comprising NaOH, KOH, LiOH, $Na_2CO_3$, $K_2CO_3$, $LiCO_3$, $CsCO_3$, NaOMe, EtOMe.

iii. In step-3, alternatively the borate ester of compound 5 is oxidatively cleaved by treating with 1 to 3 equivalents of $NaIO_4$ or $Pb(OAc)_4$ in a suitable solvent. Suitable solvent is selected from the group comprising $H_2O$, tetrahydrofuran, 1,4-dioxane, methanol, ethanol or mixtures thereof.

iv. In step-4, compound 6 is converted into Tavaborole (1) under acidic or basic conditions by dehydrative cyclization. Suitable acid is selected from the group comprising HCl, $H_2SO_4$, AcOH, HCOOH, $BF_3Et_2O$, $AlCl_3$, $BBr_3$ or the like. Suitable base is selected from the group comprising NaOH, KOH, LiOH, $Na_2CO_3$, $K_2CO_3$, $LiCO_3$, $CsCO_3$, NaOMe, EtOMe.

Tavaborole obtained by the above two syntheses is 92-95% pure. When the reaction is performed as exemplified in examples 4 and 10 supra, Tavaborole obtained is substantially pure, with purity greater than or equal to 99% and hence doesn't require further purification. Tavaborole isolated from the instant processes or from any other process can be further purified from solvents selected from the group comprising alkanes like hexanes, toluene, cyclohexane; alcohols like methanol, ethanol, IPA; water; acetonitrile; tetrahydrofuran; acetone; ethyl acetate; dichloromethane or mixtures thereof.

Tavaborole can be purified by any of the following procedures:

i. Mixing it in any of the above said suitable solvents or mixtures thereof and treating the thus obtained solution with an anti-solvent, which is water in many of the cases;

ii. Mixing Tavaborole in any of the above said solvents or mixtures, optionally heating the solution to dissolve the compound and isolating the pure compound by cooling the solution;

iii. Treating Tavaborole with silica gel in any of the above suitable solvents followed by crystallization in any of the solvents or mixtures thereof, and iv. Dissolving Tavaborole in aqueous alkali solution followed by washing with ethyl acetate, adjusting the pH of the aqueous layer to acidic with HCl, and filtering the precipitated solid.

In one aspect crude Tavaborole is dissolved in acetonitrile at 25-60° C., preferably at 45-50° C., and isolation step is performed by adding the anti-solvent water.

In the second aspect, crude Tavaborole is dissolved in mixture of IPA and toluene at 40-80° C., preferably at 60-70° C., and the pure product is isolated by cooling the solution.

In another aspect crude Tavaborole is treated with silica gel in toluene and recrystallized in hexane.

In another aspect crude Tavaborole is recrystallized from a mixture of toluene and acetonitrile solvents, which comprises the steps of dissolving the crude Tavaborole in toluene—acetonitrile mixture while heating, followed by gradual cooling during which pure Tavaborole solid precipitates.

The major process impurities which are eliminated during the purification of Tavaborole according to the present invention are depicted below (A & B), thus obtaining Tavaborole in substantially pure form with a purity greater than 99%.

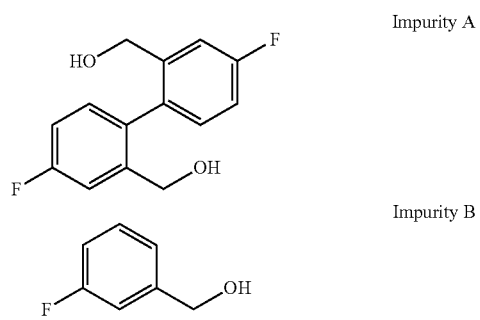

Impurity A

Impurity B

In one aspect of the invention, crystalline polymorphic forms I, II, III, IV and V of Tavaborole are reported whose X-ray diffraction pattern are represented by FIG. 1, FIG. 3, FIG. 4, FIG. 5 and FIG. 6 respectively and whose 2-theta values are tabulated in Table-1, Table-2, Table-3, Table-4 and Table-5 respectively.

The polymorphic crystalline Form I of Tavaborole may produce an X-ray diffraction pattern comprising one or more of the following reflections: 6.30, 12.66 and 25.5, +0.2°2θ or that produces an X-ray powder diffraction pattern further comprising one or more of the following reflections: 5.70, 11.43, 14.25, 14.83, 16.33, 20.31, 26.23, 26.98, 28.84, 30.95, 32.06, 33.44, 36.96, 38.71, 41.40±0.2°2θ or that produces an X-ray powder diffraction pattern comprising the 2 theta values tabulated in Table-1.

The polymorphic crystalline Form I of Tavaborole may also be identified by the DSC as depicted in FIG. 2. The X-ray diffraction pattern of Tavaborole polymorphic Form I is represented by FIG. 1.

The polymorphic crystalline Form II of Tavaborole may produce an X-ray diffraction pattern comprising one or more of the following reflections: 6.31, 14.35, 14.91, 16.44 and 27.08±0.2°2θ or that produces an X-ray powder diffraction pattern further comprising one or more of the following reflections: 12.68, 12.91, 20.41, 24.95, 25.51, 25.85, 26.33, 26.68, 27.08, 27.68, 28.93, 30.51, 31.74±0.2°2θ or that produces an X-ray powder diffraction pattern comprising the 2 theta values tabulated in Table-2. The X-ray diffraction pattern of Tavaborole polymorphic Form II is represented by FIG. 3.

The polymorphic crystalline Form III of Tavaborole may produce an X-ray diffraction pattern comprising one or more of the following reflections: 6.21, 12.55, 14.23, 14.82, 16.36, 25.37, and 26.99±0.2° 2θ or that produces an X-ray powder diffraction pattern further comprising one or more of the following reflections: 5.56, 12.88, 20.27, 24.17, 24.83, 25.37, 26.23, 26.99, 28.81, 30.05, 30.33, 30.9, 31.9, 33.37, 36.88 and 38.56±0.2° 2θ or that produces an X-ray powder diffraction pattern comprising the 2 theta values tabulated in Table-3. The X-ray diffraction pattern of Tavaborole polymorphic Form III is represented by FIG. 4.

The polymorphic crystalline Form IV of Tavaborole may produce an X-ray diffraction pattern comprising one or more of the following reflections: 6.35, 7.55, 8.25, 8.46, 14.2, 14.6, 14.9, 16.5, 25.46, 25.84, 26.38 and 26.63±0.2° 2θ or that produces an X-ray powder diffraction pattern further comprising one or more of the following reflections: 7.09, 10.23, 12.74, 13.17, 13.76, 15.27, 15.55, 17.07, 17.72, 18.15, 19.31, 19.90, 20.51, 21.88, 22.8, 23.08, 24.29, 24.92, 27.09, 27.67, 29.42, 30.19 and 31.66±0.2° 2θ or that produces an X-ray powder diffraction pattern comprising the 2 theta values tabulated in Table-4. The X-ray diffraction pattern of Tavaborole polymorphic Form IV is represented by FIG. 5.

The polymorphic crystalline Form V of Tavaborole may produce an X-ray diffraction pattern comprising one or more of the following reflections: 6.3, 7.48, 8.21, 8.37, 14.16, 14.35, 14.54, 14.88, 15.55, 16.41, 25.37, 25.78, 26.29, 26.5 and 27.03±0.2° 2θ or that produces an X-ray powder diffraction pattern further comprising one or more of the following reflections: 7.01, 10.16, 10.68, 12.64, 13.14, 15.2, 16.07, 16.67, 17.05, 17.64, 18.08, 19.88, 20.43, 22.77, 24.3, 24.87, 26.29, 27.37, 28.90, 29.39±0.2° 2θ or that produces an X-ray powder diffraction pattern comprising the 2 theta values tabulated in Table-5. The X-ray diffraction pattern of Tavaborole polymorphic Form V is represented by FIG. 6.

Generally, the crystalline forms of the present invention are prepared by contacting Tavaborole with a solvent, or mixture of solvents, one preferred method is refluxing Tavaborole in a mixture of solvents and then precipitating Tavaborole from the solvent using conventional techniques (e.g. slow or fast cooling, addition of crystallization solvent, drying at atmospheric or reduced pressure), so as to form the desired crystalline form Tavaborole.

The solvent components used in producing the crystalline forms of the present invention include methanol, ethanol, IPA, methyl tertiary butyl alcohol, toluene, acetone tetrahydrofuran, ethyl acetate, dichloromethane, acetonitrile or mixtures thereof.

According to the process of preparing crystalline Tavaborole Form I, the process comprising contacting Tavaborole with mixture of solvents; heating the solvents with Tavaborole to reflux; isolating Tavaborole by cooling the solvent to 0-5° C. and thereby obtaining the crystalline Tavaborole Form I. Suitable mixture of solvent for the preparation of crystalline tavaborole Form-I are selected from the group comprising ethyl acetate, toluene, acetonitrile, IPA.

In another embodiment,
the crystalline Form I of Tavaborole is obtained by refluxing Tavaborole in a mixture of acetonitrile and toluene and isolating Tavaborole by cooling to 0-5° C.;
the crystalline Form II of Tavaborole is obtained by the crystallizing Tavaborole from toluene or mixture of toluene and methanol;
the crystalline Form III of Tavaborole is obtained by the crystallizing Tavaborole from water or mixture of water and methanol;
the crystalline Form IV of Tavaborole is obtained by the crystallizing Tavaborole from acetone or THF or melting of solid Tavaborole Form I at 136° C. and cooling; and
the crystalline Form V of Tavaborole is obtained by crystallizing Tavaborole from ethyl acetate, dichloromethane, acetonitrile or methyl tertiary butyl ether solvents.

The X-Ray diffraction data of the Tavaborole crystalline forms obtained are tabulated below.

TABLE 1

X-ray diffraction data for Tavaborole Polymorphic Form I

| Peak no. | Angle 2θ (°) | d value Angstrom | Intensity % |
|---|---|---|---|
| 1. | 5.70 | 15.46 | 4.7 |
| 2. | 6.30 | 13.99 | 100 |
| 3. | 11.43 | 7.73 | 1.7 |
| 4. | 12.66 | 6.98 | 36 |
| 5. | 14.25 | 6.20 | 13.5 |
| 6. | 14.83 | 5.96 | 3.2 |
| 7. | 16.33 | 5.42 | 4.8 |
| 8. | 20.31 | 4.36 | 1.7 |
| 9. | 25.52 | 3.48 | 26.5 |
| 10. | 26.23 | 3.39 | 8.7 |
| 11. | 26.98 | 3.30 | 12.1 |
| 12. | 28.84 | 3.09 | 2 |
| 13. | 30.95 | 2.88 | 3.3 |
| 14. | 32.06 | 2.78 | 3.3 |
| 15. | 33.44 | 2.67 | 2.3 |
| 16. | 36.96 | 2.42 | 3.2 |
| 17. | 38.71 | 2.32 | 6.5 |
| 18. | 41.40 | 2.17 | 2.1 |

TABLE 2

X-ray diffraction data for Tavaborole Polymorphic Form II

| Peak no. | Angle 2θ (°) | d value Angstrom | Intensity % |
|---|---|---|---|
| 1. | 6.31 | 13.97 | 30 |
| 2. | 8.24 | 10.71 | 16.6 |
| 3. | 8.43 | 10.47 | 7.1 |
| 4. | 12.68 | 6.97 | 10.9 |
| 5. | 12.91 | 6.85 | 5.6 |
| 6. | 14.35 | 6.16 | 100 |
| 7. | 14.91 | 5.93 | 27.5 |
| 8. | 16.44 | 5.38 | 33 |
| 9. | 20.41 | 4.34 | 5.6 |
| 10. | 24.95 | 3.56 | 5.1 |
| 11. | 25.51 | 3.48 | 10.4 |
| 12. | 25.85 | 3.44 | 12.7 |
| 13. | 26.33 | 3.38 | 10 |
| 14. | 26.68 | 3.33 | 6.7 |
| 15. | 27.08 | 3.28 | 14.7 |
| 16. | 27.68 | 3.21 | 4.7 |
| 17. | 28.93 | 3.08 | 9.5 |
| 18. | 30.51 | 2.92 | 5.5 |
| 19. | 31.74 | 2.81 | 5.1 |

TABLE 3

X-ray diffraction data for Tavaborole Polymorphic Form III

| Peak no. | Angle 2θ (°) | d value Angstrom | Intensity % |
|---|---|---|---|
| 1. | 5.56 | 15.87 | 4.4 |
| 2. | 6.21 | 14.21 | 68.9 |
| 3. | 12.55 | 7.04 | 36.7 |
| 4. | 12.88 | 6.86 | 5.1 |
| 5. | 14.23 | 6.21 | 100 |
| 6. | 14.82 | 5.97 | 38.6 |
| 7. | 16.36 | 5.41 | 60.8 |
| 8. | 20.27 | 4.37 | 10.9 |
| 9. | 24.17 | 3.67 | 4.2 |
| 10. | 24.83 | 3.58 | 6.5 |
| 11. | 25.37 | 3.5 | 46.9 |
| 12. | 26.23 | 3.39 | 14 |
| 13. | 26.99 | 3.3 | 23.2 |

TABLE 3-continued

X-ray diffraction data for
Tavaborole Polymorphic
Form III

| Peak no. | Angle 2θ (°) | d value Angstrom | Intensity % |
|---|---|---|---|
| 14. | 28.81 | 3.09 | 12.3 |
| 15. | 30.05 | 2.97 | 4.8 |
| 16. | 30.33 | 2.94 | 9.2 |
| 17. | 30.9 | 2.89 | 9.8 |
| 18. | 31.9 | 2.8 | 5.2 |
| 19. | 33.37 | 2.68 | 4.6 |
| 20. | 36.88 | 2.434 | 7 |
| 21. | 38.56 | 2.33 | 12 |

TABLE 4

X-ray diffraction data for
Tavaborole Polymorphic
Form IV

| Peak no. | Angle 2θ (°) | d value Angstrom | Intensity % |
|---|---|---|---|
| 1. | 6.35 | 13.89 | 23.6 |
| 2. | 7.09 | 12.45 | 9.6 |
| 3. | 7.55 | 11.68 | 51.9 |
| 4. | 8.25 | 10.7 | 95.7 |
| 5. | 8.46 | 10.43 | 38.6 |
| 6. | 10.23 | 8.63 | 9.3 |
| 7. | 12.74 | 6.94 | 12.2 |
| 8. | 13.17 | 6.71 | 6.1 |
| 9. | 13.76 | 6.4 | 7.8 |
| 10. | 14.2 | 6.2 | 100 |
| 11. | 14.6 | 6.06 | 57.9 |
| 12. | 14.91 | 5.9 | 29.7 |
| 13. | 15.27 | 5.79 | 14.6 |
| 14. | 15.55 | 5.69 | 10.1 |
| 15. | 16.5 | 5.36 | 25.1 |
| 16. | 17.07 | 5.18 | 12.4 |
| 17. | 17.72 | 5 | 10.2 |
| 18. | 18.15 | 4.88 | 9.3 |
| 19. | 19.31 | 4.59 | 6 |
| 20. | 19.9 | 4.45 | 19.3 |
| 21. | 20.51 | 4.32 | 12.5 |
| 22. | 21.88 | 4.05 | 4.2 |
| 23. | 22.8 | 3.89 | 7.7 |
| 24. | 23.08 | 3.84 | 8.7 |
| 25. | 24.29 | 3.66 | 4.7 |
| 26. | 24.92 | 3.56 | 9.8 |
| 27. | 25.46 | 3.49 | 47 |
| 28. | 25.84 | 3.44 | 59 |
| 29. | 26.38 | 3.37 | 22 |
| 30. | 26.63 | 3.34 | 33.1 |
| 31. | 27.09 | 3.28 | 19.2 |
| 32. | 27.67 | 3.22 | 18.4 |
| 33. | 29.42 | 3.03 | 5.7 |
| 34. | 30.19 | 2.95 | 5.1 |
| 35. | 31.66 | 2.82 | 4.6 |

TABLE 5

X-ray diffraction data for
Tavaborole Polymorphic
Form V

| Peak no. | Angle 2θ (°) | d value Angstrom | Intensity % |
|---|---|---|---|
| 1. | 6.3 | 14.01 | 29.7 |
| 2. | 7.01 | 12.58 | 8.9 |
| 3. | 7.48 | 11.8 | 56.2 |
| 4. | 8.21 | 10.74 | 55.9 |
| 5. | 8.37 | 10.55 | 22.2 |
| 6. | 10.16 | 8.69 | 15.2 |
| 7. | 10.68 | 8.27 | 4.9 |
| 8. | 12.64 | 6.99 | 10.8 |
| 9. | 13.14 | 6.72 | 7.9 |
| 10. | 14.16 | 6.24 | 99 |
| 11. | 14.35 | 6.16 | 100 |
| 12. | 14.54 | 6.08 | 98.4 |
| 13. | 14.88 | 5.94 | 34.8 |
| 14. | 15.2 | 5.82 | 17.3 |
| 15. | 15.55 | 5.69 | 24.6 |
| 16. | 16.07 | 5.5 | 10.5 |
| 17. | 16.41 | 5.39 | 42.2 |
| 18. | 16.67 | 5.31 | 16.5 |
| 19. | 17.05 | 5.19 | 8.2 |
| 20. | 17.64 | 5.02 | 7.9 |
| 21. | 18.08 | 4.9 | 14.2 |
| 22. | 19.88 | 4.46 | 15.7 |
| 23. | 20.43 | 4.34 | 11.4 |
| 24. | 22.77 | 3.9 | 9.1 |
| 25. | 24.3 | 3.65 | 7.4 |
| 26. | 24.87 | 3.57 | 13.9 |
| 27. | 25.37 | 3.5 | 52.4 |
| 28. | 25.78 | 3.45 | 25.1 |
| 29. | 26.29 | 3.38 | 26 |
| 30. | 26.5 | 3.36 | 24.9 |
| 31. | 27.03 | 3.29 | 32.3 |
| 32. | 27.37 | 3.25 | 14.1 |
| 33. | 28.9 | 3.08 | 9.5 |
| 34. | 29.39 | 3.03 | 9 |

Definitions

The following terms shall have for the purpose of this application, including the claims appended hereto, the respective meanings set forth below:

"Hydroxyl or Hydroxy protecting groups", the terms are used synonymously, means those groups that one skilled in the field would recognize as being suitable to protect the —OH substituent on an alkyl or ringed system as described herein and which may be removed under deprotection conditions known to those skilled in the field as set forth. Non-limiting examples of hydroxy protecting groups include ether protecting groups comprising benzyl ethers, silyl ethers, alkyl ethers including methyl ethers, ethyl ethers, propyl ethers, butyl ethers or the like; esters including benzoate, acetate or the like; acetals including MOP, BOM, THP or the like. Suitable acyl protecting agents used are selected from the group comprising of acetyl chloride, acetic anhydride, benzoyl chloride or the like; Suitable Silyl protecting agents used is selected from a group comprising of trimethyl silyl chloride, triethyl silyl chloride, and tertiary butyl dimethyl silyl chloride (TBDMSCl) or the like. In one aspect of the invention, the silyl protecting group employed is TBDMSCl.

Suitable Transition Metal catalysts that can be employed in the present invention are Pd catalyst or Ni catalysts. The Pd catalyst is selected from the group comprising of $PdCl_2(dppf)$, $[PdCl_2dppf].CH_2Cl_2$, $PdCl_2(PPh_3)_2$, $Pd(PPh_3)_4$, $Pd(OAc)_2$, $[Pd_2dba_3]$, $[Pd(allyl)Cl]_2$, $Pd(acac)_2$, $PhPd(OAc)(PPh)_2$ any Palladium catalyst that generates in situ Pd(0) and combinations thereof. In one aspect of the invention, Pd catalyst used is $PdCl_2(dppf)$. Non limiting examples of Ni catalyst selected from group of $NiCl_2(dppp)$, $NiCl_2(dppf)$, $NiCl_2(dppe)$, $NiCl_2.glyme$, $NiBr_2.glyme$, $NiCl_2(PPh_3)_2$, NiCl$_2$(PCy$_3$)$_2$, Ni(PPh$_3$)$_4$, Ni(COD)$_2$, NiCl$_2$, NiBr$_2$ or any Nickel catalyst that generates in situ Ni(0) and combinations thereof. In one aspect of the invention, Ni catalyst used is NiCl$_2$(dppp).

Appropriate ligand is selected from the group comprising of Xphos, MeO-CM-Phos, Sphos, DavePhos, RuPhos, tBu$_3$P—HBF$_4$, QPhos, JohnPhos, Me$_4$-tBu-XPhos, Ad$_2$PBu, BrettPhos, AmPhos, PPh$_3$, tri(o-tolyl) phosphine or the like. In one aspect of the invention, the ligand used is tri(o-tolyl)phosphine.

Suitable borylation reagent used is selected from the group comprising of boronic acids, Bis(neopentyl glycolato) diboron, Bis(catecholato)diboron, Bis(hexylene glycolato) diboron, Bis(pinacolato)diboron, Tetrahydroxydiboron, Pinacolborane, Methylpentanediolborane, Catecholborane, Neopentylglycoborane, Trialkyl borate. In one aspect of the invention, borylation reagent used is Bis(pinacolato)diboron.

Suitable base that can be employed in step 2 of Scheme-1 is an organic base or an inorganic base. Suitable inorganic base used is selected from the group comprising of KOPh, KOAc, NaOAc, NH$_4$OAc, Cu(OAc)$_2$, Cs$_2$CO$_3$, K$_2$CO$_3$, Na$_2$CO$_3$, Ag$_2$CO$_3$, K$_3$PO$_4$, NaOH, KOH, CsOH, KOMe, NaOMe, LiOtBu, NaOtBu, KOtBu or the like. In one aspect of the invention, the inorganic base used is KOAc. Suitable organic base used is selected from the group comprising of pyridine, triethyl amine, leutidine, DABCO, DBU, 1,2,2,6,6-pentamethylpipiridine, 1,1,3,3-tetramethylguanidine, iPr$_2$NEt, NBu$_3$, Cy$_2$NMe or the like. In one aspect of the invention, suitable organic base used is iPr$_2$Net.

"hydroxyl deprotecting agents or deprotecting agents" means those reagents that one skilled in the field would recognize as being suitable to remove the protecting groups of a hydroxyl moiety as described herein. Suitable hydroxyl deprotecting agents may be acid or base. Non-limiting examples being inorganic bases like potassium hydroxide, lithium hydroxide, sodium hydroxide, potassium carbonate, sodium carbonate or the like; metal alkoxides like sodium methoxide, sodium ethoxide; metal carbonates like sodium carbonate, potassium carbonate, cesium carbonate or the like; acid deprotecting agent selected from the group comprising HCl, H$_2$SO$_4$, HNO$_3$, AcOH, HCOOH, BF$_3$Et$_2$O, AlCl$_3$, BBr$_3$ or the like.

These deprotecting agents are most suitable for simultaneously removing the boronate ester protecting groups.

Additive or co-catalyst that is employed is selected from the group comprising Cu(OTf)$_2$, Cu(OAc)$_2$, CuCl, CuBr, CuI, ZnCl$_2$, Ag$_2$CO$_3$ or the like.

The dehydrating agent used for the cyclization of Tavaborole is an organic or an inorganic acid selected from the group comprising HCl, H$_2$SO$_4$, HNO$_3$, AcOH, HCOOH, BF$_3$Et$_2$O, AlCl$_3$, BBr$_3$ or the like. HCl being the most preferred acid. The base employed for cyclization of Tavaborole is selected from the group comprising NaOH, KOH, LiOH, Na$_2$CO$_3$, K$_2$CO$_3$, LiCO$_3$, CsCO$_3$, NaOMe, EtOMe.

| Reagent Name | Definition |
| --- | --- |
| NBS | N-Bromosuccinimide |
| Pd | Palladium |
| MOP | Methoxypropyl acetal |
| BOP | Benzyloxymethyl acetal |
| TBDMSCl | tert-Butyldimethylsilyl chloride |
| n-BuLi | n-Butyllithium |
| BF$_3$Et$_2$O | Boron trifluoride etherate |
| NaIO$_4$ | Sodium periodate |
| Pb(OAc)$_4$ | Lead tetraacetate |
| [PdCl$_2$dPPf]•CH$_2$Cl$_2$ | [1,1'-Bis(diphenylphosphino)ferrocene]dichloro palladium(II), complex with dichloromethane |
| PdCl$_2$(PPh$_3$)$_2$ | Dichlorobis(triphenylphosphine)palladium(II) |
| Pd(PPh$_3$)$_4$ | Tetrakis(triphenylphosphine)palladium(0) |
| Pd(OAc)$_2$ | Palladium(II) acetate |
| [Pd$_2$dba$_3$] | Tris(dibenzylideneacetone)dipalladium |
| [Pd(allyl)Cl]$_2$ | Allylpalladium(II) chloride dimer |
| Pd(acac)$_2$ | Palladium(II) acetylacetonate |
| PhPd(OAc)(PPh$_3$)$_2$ | Bis(triphenylphosphine)phenyl palladium acetate |
| PdCl$_2$(dppf) | [1,1'-Bis(diphenylphosphino)ferrocene] dichloropalladium(II) |
| NiCl$_2$(dppp) | Dichloro[1,3-bi s(diphenylphosphino)propane]nickelc |
| NiCl$_2$(dppf) | [1,1'-Bis(diphenylphosphino)ferrocene]dichloronickel(II) |
| NiCl$_2$(dppe) | 1,2-Bis(diphenylphosphino)ethane nickel(II) chloride |
| NiCl$_2$•glyme | dichloronickel;1,2-dimethoxyethane |
| NiBr$_2$•glyme | Nickel(II) bromide 2-methoxyethyl ether complex |
| NiCl$_2$(PPh$_3$)$_2$ | Bis(triphenylphosphine)nickel(II) dichloride |
| NiCl$_2$(PCy$_3$)$_2$ | Bis(tricyclohexylphosphine)nickel(II) chloride |
| Ni(PPh$_3$)$_4$ | Tetrakis(triphenylphosphine)nickel(0) |
| Ni(COD)$_2$ | Bis(cyclooctadiene)nickel(0) |
| NiCl$_2$ | Nickel(II) chloride |
| NiBr$_2$ | Nickel(II) bromide |
| Xphos | 2-Dicyclohexylphosphino-2',4',6'-triisopropylbiphenyl |
| MeO-CM-Phos | N-Methyl-2-(2'-dicylohexylphosphino-5'-methoxyphenyl)indole |
| Sphos | 2-Dicyclohexylphosphino-2',6'-dimethoxybiphenyl |
| DavePhos | 2-Dicyclohexylphosphino-2'-(N,N-dimethylamino)biphenyl |
| RuPhos | 2-Dicyclohexylphosphino-2',6'-diisopropoxybiphenyl |
| tBu$_3$P-HBF$_4$ | Tributylphosphonium tetrafluoroborate |
| QPhos | 1,2,3,4,5-Pentaphenyl-1'-(di-tert-butylphosphino)ferrocene |
| JohnPhos | (2-Biphenyl)di-tert-butylphosphine, (2-Biphenylyl)di-tert-butylphosphine |
| Me$_4$-tBu-XPhos | 2-Di-tert-butylphosphino-3,4,5,6-tetramethyl-2',4',6'-triisopropyl-1,1'-biphenyl |
| Ad$_2$PBu | di(1-adamantyl)-n-butylphosphine |
| BrettPhos | 2-(Dicyclohexylphosphino)3,6-dimethoxy-2',4',6'-triisopropyl-1,1'-biphenyl |

-continued

| Reagent Name | Definition |
| --- | --- |
| AmPhos | Bis(di-tert-butyl(4-dimethylaminophenyl)phosphine) |
| PPh$_3$ | Triphenylphosphine |
| KOPh | Potassium phenoxide |
| KOAc | Potassium acetate |
| NaOAc | Sodium acetate |
| NH$_4$OAc | Ammonium acetate |
| Cu(OAc)$_2$ | Copper(II) acetate |
| Cs$_2$CO$_3$ | Caesium carbonate |
| K$_2$CO$_3$ | Potassium carbonate |
| Na$_2$CO$_3$ | Sodium carbonate |
| Ag$_2$CO$_3$ | Silver carbonate |
| K$_3$PO$_4$ | Tripotassium phosphate |
| NaOH | Sodium hydroxide |
| KOH | Potassium hydroxide |
| CsOH | Cesium hydroxide |
| KOMe | Potassium methoxide |
| NaOMe | Sodium methoxide |
| LiOtBu | Lithium tert-butoxide |
| NaOtBu | Sodium-t-butoxide |
| KOtBu | Potassium tert-butoxide |
| DABCO | 1,4-diazabicyclo[2.2.2]octane |
| DBU | 1,8-Diazabicyclo[5.4.0]undec-7-ene |
| iPr$_2$NEt | N,N-Diisopropylethylamine |
| NBu$_3$ | N-tributylamine |
| Cy$_2$NMe | N,N-Dicyclohexylmethylamine |
| HNO$_3$ | Nitric acid |
| Cu(OTf)$_2$ | Copper (II) triflate |
| Cu(OAc)$_2$ | Copper(II) acetate |
| CuCl | Copper(I) chloride |
| CuBr | Copper(I) bromide |
| CuI | Copper(I) iodide |
| ZnCl$_2$ | Zinc chloride |
| AlCl$_3$ | Aluminium chloride |
| BBr$_3$ | Boron tribromide |
| Ag$_2$CO$_3$ | Silver carbonate |
| NaHCO$_3$ | Sodium hydrogen carbonate |
| LiCO$_3$ | Lithium carbonate |
| LiOH | Lithium hydroxide |
| Na$_2$SO$_4$ | Sodium sulfate |
| H$_2$O | Water |
| CH$_2$Cl$_2$ | Dichloromethane |
| MTBE | Methyl tert-butyl ether |
| IPA | Isopropyl alcohol |
| MeOH | Methanol |
| EtOH | Ethanol |
| EtOAc | Ethyl acetate |
| CCl$_4$ | Carbon tetrachloride |
| HCl | Hydrochloric acid |
| H$_2$SO$_4$ | Sulfuric acid |
| AcOH | Acetic acid |
| HCOOH | Formic acid |
| Ac | Acetyl |

The following examples further illustrate the present invention, but should not be construed in any way as to limit its scope.

Example-1

Preparation of 2-bromo-5-fluorobenzyl acetate (3a)

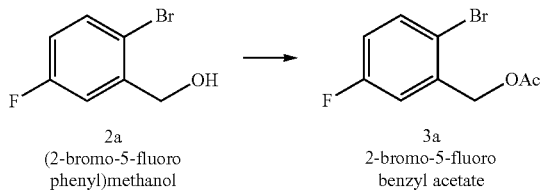 [SMILES: OCc1cc(F)ccc1Br ; CC(=O)OCc1cc(F)ccc1Br]

2a
(2-bromo-5-fluoro
phenyl)methanol 3a
2-bromo-5-fluoro
benzyl acetate

Wherein in compound 2, X=Br and in compound 3, $R^1$=Ac

To a solution of (2-bromo-5-fluorophenyl)methanol (10.25 g, 0.05 mol) and acetic anhydride (7.1 mL; 0.075 mol) in dichloromethane (50 mL) two drops of pyridine is added and the mixture is stirred at room temperature until complete disappearance of starting material (reaction is monitored by TLC). After completion, the reaction mixture is quenched with water (100 ml), and the mixture is extracted by dichloromethane (120 mL). The organic layer is separated, and washed with saturated NaHCO$_3$ (100 mL), 0.1 N HCl (50 mL) and water (100 mL) and dried over Na$_2$SO$_4$. Evaporation of the solvent gave 2-bromo-5-fluorobenzyl acetate (Yield: 97%; Purity: 99.3%).

Example-2

Preparation of 5-fluoro-2-(4,4,5,5-tetramethyl-1,3,2-dioxaborolan-2-yl) benzyl acetate (4a)

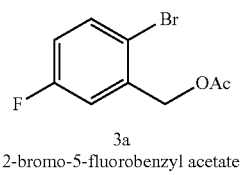

3a
2-bromo-5-fluorobenzyl acetate

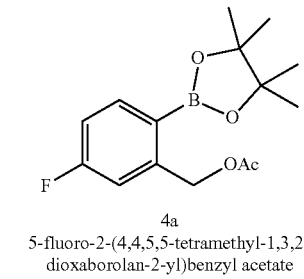

4a
5-fluoro-2-(4,4,5,5-tetramethyl-1,3,2-dioxaborolan-2-yl)benzyl acetate

Wherein in compound 4, $R^1$=Ac, $R^2$ & $R^3$ together=borate ester

To a solution of 2-bromo-5-fluorobenzyl acetate (5 g, 0.02 mol) in 1,4-dioxane (60 mL), bis(pinacolato)diboron (5.6 g, 0.022 mol) and potassium acetate (5.6 g, 0.06 mol) are added.

The resulting mixture is degassed using a stream of nitrogen and to this is added [1,1'-bis(diphenylphosphino)ferrocene]dichloropalladium(II) (250 mg, 0.34 mmol). The reaction mixture is then heated at 80° C. for 10 hrs. The mixture is cooled to room temperature, diluted with $H_2O$ and extracted with EtOAc. The organic layer is dried over $Na_2SO_4$ and evaporated in vacuo to yield 5-fluoro-2-(4,4,5,5-tetramethyl-1,3,2-dioxaborolan-2-yl) benzyl acetate that is used in the next reaction step without further purification (Yield: 95%; Purity: 99.9%).

Example-3

Preparation of 5-fluoro-1,3-dihydro-1-hydroxy-2,1-benzoxaborole (Tavaborole 1)

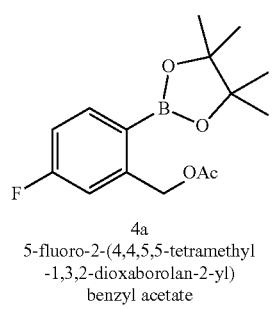

4a
5-fluoro-2-(4,4,5,5-tetramethyl-1,3,2-dioxaborolan-2-yl) benzyl acetate

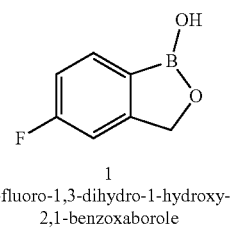

1
5-fluoro-1,3-dihydro-1-hydroxy-2,1-benzoxaborole

A mixture of 5-fluoro-2-(4,4,5,5-tetramethyl-1,3,2-dioxaborolan-2-yl) benzyl acetate (3 g) and HCl (4N HCl, 30 mL) is stirred at 80° C. for 10 hrs. Water is added, and the mixture is extracted with ethyl acetate. The organic layer is washed with water (until water layer becomes neutral), dried over $Na_2SO_4$ and evaporated in vacuo to yield 5-fluoro-1,3-dihydro-1-hydroxy-2,1-benzoxaborole (Yield: 93%; Purity: 92%).

Example-4

Preparation of 5-fluoro-1,3-dihydro-1-hydroxy-2,1-benzoxaborole (Tavaborole 1)

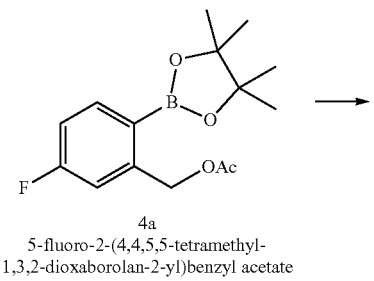

4a
5-fluoro-2-(4,4,5,5-tetramethyl-1,3,2-dioxaborolan-2-yl)benzyl acetate

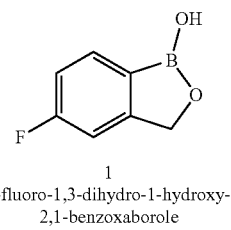

1
5-fluoro-1,3-dihydro-1-hydroxy-2,1-benzoxaborole

To a solution of 5-fluoro-2-(4,4,5,5-tetramethyl-1,3,2-dioxaborolan-2-yl)benzyl acetate (5 g) in Methanol (40 mL), NaOH (2 eq) is added and stirred for 4 hrs at RT. Solvent is removed at reduced pressure. The obtained crude is taken in mixture of THF (30 mL) and water (15 mL), and treated with concentrated HCl (7.5 ml). After completion of the reaction (usually completes in 12 hrs at RT), product is extracted with ethyl acetate and concentrated at reduced pressure to give the solid. The obtained compound is dissolved in aqueous NaOH solution (30 mL, 1 eq NaOH), washed with ethyl acetate, then acidified with aqueous HCl. The precipitated white solid is filtered, washed with water and dried (Yield: 80%; Purity: 99.8%).

Example-5

Preparation of 2-(acetoxymethyl)-4-fluorophenylboronic acid (6A)

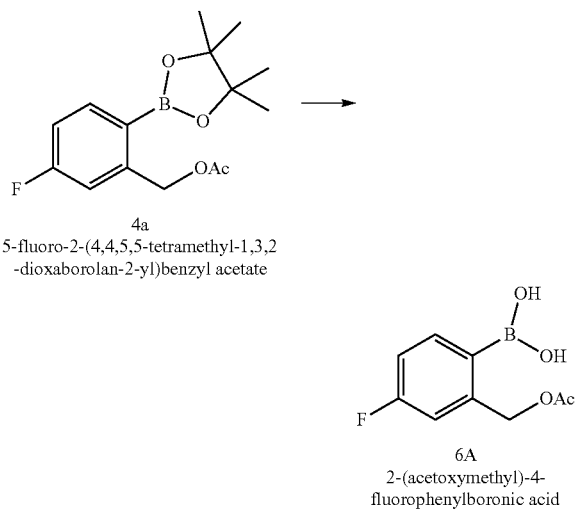

4a
5-fluoro-2-(4,4,5,5-tetramethyl-1,3,2-dioxaborolan-2-yl)benzyl acetate 6A
2-(acetoxymethyl)-4-fluorophenylboronic acid To a solution of 5-fluoro-2-(4,4,5,5-tetramethyl-1,3,2-dioxaborolan-2-yl)benzyl acetate (5.13 g, 0.014 mol) in Acetone (50 mL), sodium periodate (8.9 g, 0.042 mol), ammonium acetate (2.4 g, 0.031 mol) in water is added. After stirring at room temperature for 10 hr, 2.5N HCl (40 mL) is added, and the mixture is stirred at 0-5° C. for 20 minutes. Water is added, and the mixture is extracted with ethyl acetate. The organic layer is washed with brine and dried on anhydrous sodium sulfate. The solvent is removed under reduced pressure, and the residue is treated with MTBE to afford 2-(acetoxymethyl)-4-fluorophenylboronic acid (Yield: 83%; Purity: 94%.

Example-6

Preparation of 5-fluoro-1,3-dihydro-1-hydroxy-2,1-benzoxaborole (Tavaborole 1)

6A
2-(acetoxymethyl)-4-fluorophenylboronic acid 1
5-fluoro-1,3-dihydrobenzo[c][1,2]oxaborole A mixture of 2-(acetoxymethyl)-4-fluorophenylboronic acid (3 g) and HCl (4N HCl, 30 mL) is stirred at 80° C. for 10 hrs. Water is added, and the mixture is extracted with ethyl acetate. The organic layer is washed with water (until water layer becomes neutral), dried over $Na_2SO_4$ and evaporated in vacuo to yield 5-fluoro-1,3-dihydrobenzo[c][1,2]oxaborole (Yield: 93%; Purity: 92%).

Example-7

Preparation of (5-fluoro-2-(4,4,5,5-tetramethyl-1,3,2-dioxaborolan-2-yl)phenyl)methanol(5)

2a
(2-bromo-5-fluorophenyl)methanol 5a
(5-fluoro-2-(4,4,5,5-tetramethyl-1,3,2-dioxaborolan-2-yl)phenyl)methanol To a solution of (2-bromo-5-fluorophenyl) methanol (5 g, 0.02 mol) in 1,4-dioxane (60 mL), bis(pinacolato)diboron (5.6 g, 0.022 mol) and potassium acetate (5.6 g, 0.06 mol) were added. The resulting mixture was degassed using a stream of nitrogen and to this was added [1,1'-bis(diphenylphosphino) ferrocene]dichloropalladium(II) (250 mg, 0.34 mmol). The reaction mixture was then heated at 80° C. for 10 hrs. The mixture was cooled to room temperature, diluted with $H_2O$ and extracted with EtOAc. The organic layer was dried over $Na_2SO_4$ and evaporated in vacuum to yield (5-fluoro-2-(4,4,5,5-tetramethyl-1,3,2-dioxaborolan-2-yl) phenyl)methanol that was used in the next reaction step without further purification. Yield-95%; Purity-99.9%.

Example-8

Preparation of (4-fluoro-2-(hydroxymethyl)phenyl)boronic acid (6)

2a
(2-bromo-5-fluorophenyl)methanol 6
(4-fluoro-2-(hydroxymethyl)phenyl)boronic acid To a solution of (2-bromo-5-fluorophenyl) methanol (10.05 g, 0.049 mol) in Ethanol 100 mL), $NiCl_2$(dppp) (2.67 g, 0.0049 mol), $(HO)_2B$—$B(OH)_2$ (6.62 g, 0.074 mol), $PPh_3$ (0.01 mol), (DIPEA (25.7 mL, 0.148 mol) are added. The resulting mixture is degassed using a stream of nitrogen. The reaction mixture is stirred at reflux for 4 hrs, then cooled to room temperature, diluted with $H_2O$ and extracted with EtOAc. The organic layer is dried over $Na_2SO_4$ and evaporated in vacuo to yield (4-fluoro-2-(hydroxymethyl)phenyl)

Example-9

Preparation of 4-fluoro-2-(hydroxymethyl)phenylboronic acid (6)

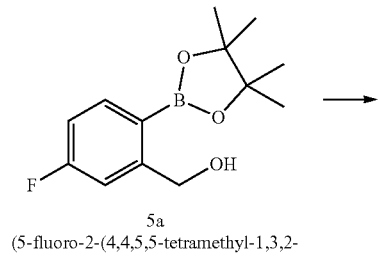

5a
(5-fluoro-2-(4,4,5,5-tetramethyl-1,3,2-dioxaborolan-2-yl)phenyl)methanol

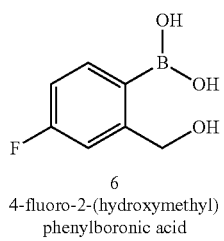

6
4-fluoro-2-(hydroxymethyl) phenylboronic acid

Wherein compound-5, $R^2$ & $R^3$=borate ester

To a solution of 5-fluoro-2-(4,4,5,5-tetramethyl-1,3,2-dioxaborolan-2-yl)phenyl)methanol (5.0 g, 0.02 mol) in Acetone (50 mL), sodium periodate (10.6 g, 0.05 mol), ammonium acetate (2.7 g, 0.035 mol) in water is added. After stirring at room temperature for 10 hr, the reaction mass is concentrated to give crude 4-fluoro-2-(hydroxymethyl)phenylboronic acid (Yield: 80%; Purity: 95%).

Example-10

Preparation of 5-fluoro-1,3-dihydro-1-hydroxy-2,1-benzoxaborole (Tavaborole 1)

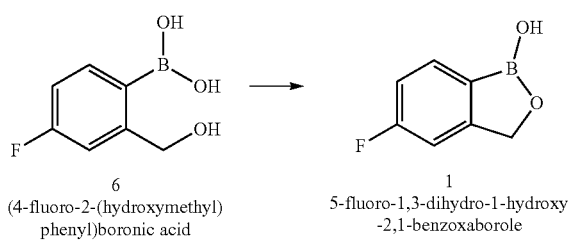 [SMILES: OCc1cc(F)ccc1B(O)O ; OB1OCc2cc(F)ccc21]

6
(4-fluoro-2-(hydroxymethyl) phenyl)boronic acid 1
5-fluoro-1,3-dihydro-1-hydroxy-2,1-benzoxaborole A mixture of crude (4-fluoro-2-(hydroxymethyl) phenyl) boronic acid (3 g) and 10% $H_2SO_4$ solution (20 mL) is stirred at room temperature for 4 hrs. Water is added, and the mixture is extracted with ethyl acetate. The organic layer is washed with brine and dried on anhydrous sodium sulfate. The solvent is removed under reduced pressure, and the residue is treated with MTBE to afford benzo[c][1,2]oxaborole-1,5(3H)-diol (Yield: 81%; Purity: 95%).

Example-11

Preparation of 5-fluorobenzo[c][1,2]oxaborol-1 (3H)-ol (Tavaborole 1)

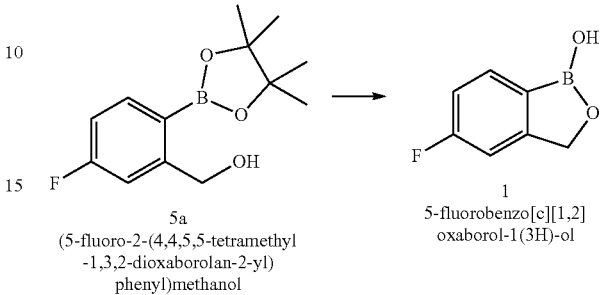

5a
(5-fluoro-2-(4,4,5,5-tetramethyl -1,3,2-dioxaborolan-2-yl) phenyl)methanol 1
5-fluorobenzo[c][1,2] oxaborol-1(3H)-ol To a solution of 5-fluoro-2-(4,4,5,5-tetramethyl-1,3,2-dioxaborolan-2-yl)phenyl methanol (5 g) in 1,4-dioxane (30 mL) and water (15 mL), and treated with concentrated HCl (7.5 ml). After completion of the reaction (usually completes in 5-6 hrs at RT), product is extracted with ethyl acetate and concentrated at reduced pressure to give the solid. The obtained compound is dissolved in aqueous NaOH solution (30 mL, 1 eq NaOH), washed with ethyl acetate, then acidified with aqueous HCl. The precipitated white solid is filtered, washed with water and dried (Yield: 77%; Purity: 99.6%).

Example-12

Purification of Tavaborole (1)

a. Crude Tavaborole is treated with a mixture of IPA:ethyl acetate (3:4) at 60-65° C., then cooled to 0-5° C. sand maintained for 1 hr. Solid is filtered under vacuum, washed with 0.5 volumes of chilled 3:4 mixture of IPA and ethyl acetate solution. The resulting solid is dried under vacuum (Yield: 77%; Purity: 99.5%).

b. Crude Tavaborole is dissolved in mixture of toluene:IPA (5:1; 6 V) at 60° C., the obtained clear solution is slowly allowed to room temperature, then cooled to 0-5° C., filtered and dried (Yield 53%; Purity 99.2%).

c. Crude Tavaborole is dissolved in mixture of toluene:acetonitrile (4:2; 6 V) at 70-80° C., the obtained clear solution is slowly allowed to room temperature, then cooled to 0-5° C., filtered and dried (Yield 81%; Purity: 99.9%).

d. Crude Tavaborole is treated with a mixture of ethanol:water (1:5) at 50-60° C., then cooled to 0-5° C. and maintained for 4 hrs. Solid is filtered, washed with 1 volume of chilled 1:5 mixture of IPA and water solution. The resulting solid is dried under vacuum (Yield: 78%; Purity: 99.7%).

e. Crude Tavaborole is dissolved in acetonitrile (2V) at 50° C. and water (20 V) is added drop wise. The solution is slowly allowed to reach room temperature, then cooled to 0-5° C., filtered, washed with a chilled mixture of acetonitrile:water; 1:10 (1V) and dried (Yield: 62%; Purity: 99.96%).

Example-13

Preparation of Tavaborole Polymorphic Forms a. Preparation of Tavaborole Form I:

To 5.0 g of Tavaborole is added 13 ml of toluene and the mixture is heated at reflux conditions to attain clear solution. To this 1.0 ml of acetonitrile is added and cooled to 25-30° C. The solution is further cooled 0-5° C. and then stirred for 1.0 hr and the solid is filtered under vacuum, dried at 25-30° C. for overnight to get crystalline Tavaborole polymorphic Form I.

b. Preparation of Tavaborole Form II:

In 100 ml round bottom flask equipped with a reflux condenser, Tavaborole 2.0 g and toluene 5.0 ml are charged at 25-30° C., the solution is heated to 50-57° C. to get a clear solution and then cooled to 25-30° C. The solution is further cooled to 0-5° C. and the resulting solid (320 mg) is filtered, washed with chilled toluene and dried under vacuum to get crystalline Tavaborole Form II.

c. Preparation of Tavaborole Form III:

In 100 ml of round bottom flask equipped with a reflux condenser, Tavaborole 2.0 g and 10 ml of water are charged and heated to reflux at 97° C. The solution is cooled to 25-30° C. and further to 0-15° C. The precipitated solid is filtered (1.4 g) and washed with water, filtered and dried under vacuum to get crystalline Tavaborole Form III.

d. Preparation of Tavaborole Form IV:

In a 100 ml round bottom flask equipped with a reflux condenser, Tavaborole (1.0 g) and 2.0 ml of acetone are charged and stirred to get clear solution. To this 18 ml of acetone is added and concentrated on rotatory evaporator. The solid that is scratched (0.62 g) from the wall of the round bottom flask after removal of entire solvent is crystalline Tavaborole Form IV.

The above Form IV can be obtained by melting polymorphic Form I of Tavaborole at 136° C. and cooling down to 25-30°.

e. Preparation of Tavaborole Form V:

In a 100 ml round bottom flask, Tavaborole (1.0 g) and 3.0 ml of methyl tertiary butyl ether are charged and the mixture is stirred to get clear solution at 25-30° C. The solution is concentrated using rotatory evaporator to obtain Tavaborole as crystalline Form V.

Alternative Routes:

Example-14

Preparation of tert-butyl((5-fluoro-2-iodobenzyl) oxy) dimethylsilane (3b)

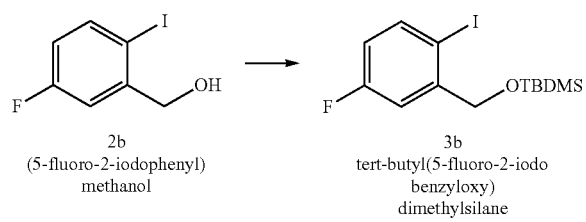 [SMILES: OCc1cc(F)ccc1I ; CC(C)(C)[Si](C)(C)OCc1cc(F)ccc1I]

2b
(5-fluoro-2-iodophenyl) methanol 3b
tert-butyl(5-fluoro-2-iodo benzyloxy) dimethylsilane Wherein in compound 2, X=I and in compound 3, $R^1$=TBDMS To a solution of (5-fluoro-2-iodophenyl)methanol (3.78 g, 0.015 mol) in $CH_2Cl_2$ (40 mL), imidazole (3.0 g, 0.045 mol) and TBDMS chloride (2.5 g, 0.016 mol) are added successfully, the reaction mass is stirred at room temperature for 8 hrs. After completion, reaction mass is quenched with water, washed with brine solution, extracted with $CH_2Cl_2$, and the organic layer is dried over $Na_2SO_4$, and concentrated to give tert-butyl((5-fluoro-2-iodobenzyl)oxy)dimethylsilane (Yield-88%).

Example-15

Preparation of tert-butyl((5-fluoro-2-(4,4,5,5-tetramethyl-1,3,2-dioxaborolan-2-yl)benzyl)oxy)dimethylsilane (4b)

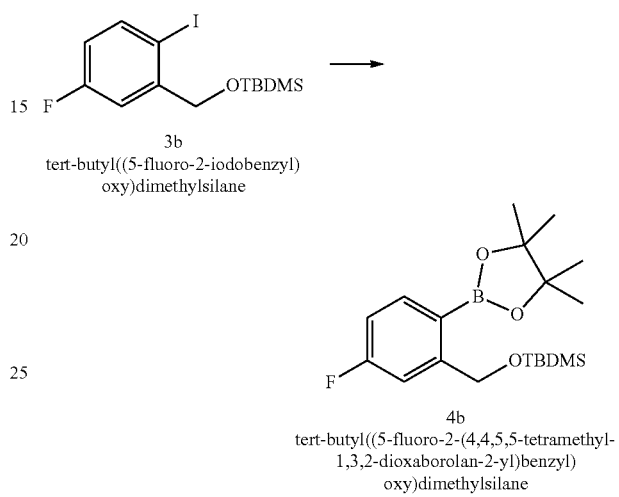

3b
tert-butyl((5-fluoro-2-iodobenzyl) oxy)dimethylsilane 4b
tert-butyl((5-fluoro-2-(4,4,5,5-tetramethyl-1,3,2-dioxaborolan-2-yl)benzyl) oxy)dimethylsilane Wherein in compound 4, $R^1$=TBDMS, $R^2$ & $R^3$ together=borate ester To a solution of tert-butyl((5-fluoro-2-iodobenzyl)oxy) dimethylsilane (4.76 g, 0.013 mol) in Acetonitrile (40 mL), $Pd(OAc)_2$ (292 mg, 0.0013 mol), Tri-O-tolylphosphine (395 mg, 0.0013 mol), Bis(pinacolato)diboron (4.98 g, 0.0196 mol), $Cs_2CO_3$ (6.39 g, 0.0196 mol), CuI (0.49 g, 0.0026 mol) are added. The resulting mixture is degassed using a stream of nitrogen. The reaction mixture is stirred at room temperature for 36 hrs. The mixture is cooled to room temperature, diluted with $H_2O$ and extracted with EtOAc (120 mL). The organic layer is dried over $Na_2SO_4$ and evaporated in vacuo to yield tert-butyl((5-fluoro-2-(4,4,5,5-tetramethyl-1,3,2-dioxaborolan-2-yl)benzyl)oxy)dimethylsilane and that is used in the next reaction step without further purification (Yield-87%).

Example-16

Preparation of 5-fluoro-1,3-dihydro-1-hydroxy-2,1-benzoxaborole (Tavaborole 1)

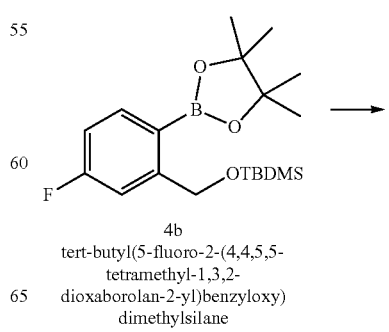

4b
tert-butyl(5-fluoro-2-(4,4,5,5-tetramethyl-1,3,2-dioxaborolan-2-yl)benzyloxy) dimethylsilane

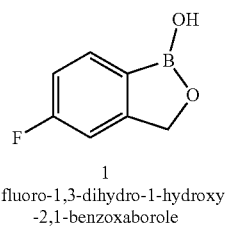

1
5-fluoro-1,3-dihydro-1-hydroxy
-2,1-benzoxaborole

To a solution of tert-butyl((5-fluoro-2-(4,4,5,5-tetramethyl-1,3,2-dioxaborolan-2-yl)benzyl)oxy)dimethylsilane (5.13 g, 0.014 mol) in Acetone (50 mL), sodium periodate (8.9 g, 0.042 mol), ammonium acetate (2.4 g, 0.031 mol) in water is added. After stirring at room temperature for 10 hr, 2.5N HCl (40 mL) is added, and the mixture is stirred at room temperature overnight. Water is added, and the mixture is extracted with ethyl acetate. The organic layer is washed with brine and dried on anhydrous sodium sulfate. The solvent is removed under reduced pressure, and the residue is treated with MTBE to afford 5-fluoro-1,3-dihydro-1-hydroxy-2,1-benzoxaborole (Yield: 83%; Purity: 94%).

We claim:

1. A process for preparation of 5-fluoro-1,3-dihydro-1-hydroxy-2,1-benzoxaborole (Tavaborole) comprising the steps of:
   (i) protecting primary hydroxyl moiety of compound 2 with a hydroxyl protecting agent to obtain hydroxyl protected compound 3;

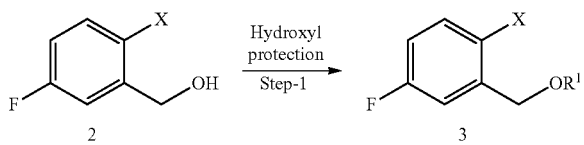

(ii) converting the hydroxyl protected compound 3 into a borate compound 4 using a borylation reagent via a transition metal catalyzed cross-coupling reaction; and

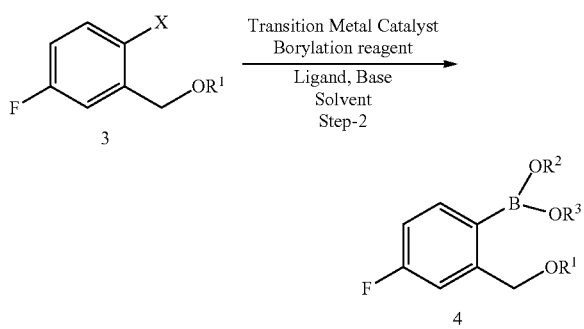

(iii) converting the borate compound 4 into Tavaborole;
   Wherein
   X is a member selected from Br, I, OTf;
   $R^1$ is hydroxyl protecting group or hydrogen; and
   $R^2$, $R^3$ are members independently selected from H; substituted or unsubstituted $C_1$-$C_8$ alkyl; substituted or unsubstituted heteroalkyl $C_1$-$C_8$, substituted or unsubstituted aryl $C_5$-$C_{10}$; substituted or unsubstituted heteroaryl $C_5$-$C_{10}$; substituted or unsubstituted cycloalkyl $C_3$-$C_8$; substituted or unsubstituted heterocycloalkyl $C_3$-$C_8$; together with the atoms to which they are attached may be optionally joined to form a 4- to 8-membered ring.

2. The process as claimed in claim 1, wherein borate compound 4 in step (iii) is converted into Tavaborole by simultaneous or sequential deprotection of hydroxyl protecting group and boronate ester group of compound 4 using a hydroxyl deprotecting agent followed by cyclization in presence of an acid or a base.

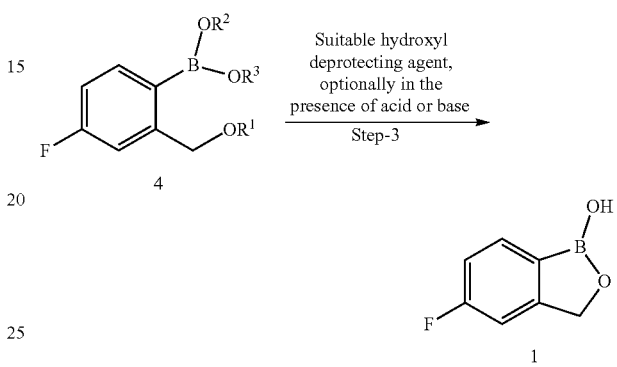

3. The process as claimed in claim 1, wherein the hydroxyl protecting agent comprises acyl protecting agent selected from the group consisting of acetyl chloride, acetic anhydride, and benzoyl chloride; or Silyl protecting agents selected from the group consisting of trimethyl silyl chloride, triethyl silyl chloride, and tertiary butyl dimethyl silyl chloride (TBDMSCl).

4. The process as claimed in claim 1, wherein transition metal catalyzed cross-coupling reaction of step (ii) is carried out in presence of Pd catalyst selected from $PdCl_2$(dppf), [$PdCl_2$dppf]$CH_2Cl_2$, $PdCl_2(PPh_3)_2$, $Pd(PPh_3)_4$, $Pd(OAc)_2$, [$Pd_2dba_3$], [Pd(allyl)Cl]$_2$pd(acac)$_2$, PhPd(OAc)(PPh)$_2$ or any Palladium catalyst that generates in situ Pd(0) and combinations thereof; or Ni catalyst selected from $NiCl_2$(dppp), $NiCl_2$(dppf), $NiCl_2$(dppe), $NiCl_2$.glyme, $NiBr_2$.glyme, $NiCl_2(PPh_3)_2$, $NiCl_2(PCy_3)_2$, $Ni(PPh_3)_4$, $Ni(PPh_3)_4$, $Ni(COD)_2$, $NiCl_2$, $NiBr_2$ or any Nickel catalyst that generates in situ Ni(0) and combinations thereof.

5. The process as claimed in claim 1, wherein the reaction of step (ii) is carried out in presence of a solvent selected from toluene, xylene, N,N-dimethylformamide, dimethylsulfoxide, tetrahydrofuran and 1,4-dioxane or mixtures thereof; and wherein the borylation reagent is selected from the group consisting of Bis(neopentylglycolato)diboron, Bis(catecholato)diboron, Bis(hexyleneglycolato)diboron, Bis(pinacolato)diboron, Tetrahydroxydiboron, Pinacolborane, Methylpentanediolborane, Catecholborane, Neopentylglycoborane and Trialkyl borate.

6. The process as claimed in claim 1, wherein the reaction of step (ii) is carried out in presence of a ligand selected from the group consisting of Xphos, MeO-CM-Phos, Sphos, DavePhos, RuPhos, $tBu_3P$—$HBF_4$, QPhos, JohnPhos, $Me_4$-tBu-XPhos, $Ad_2PBu$, BrettPhos, AmPhos, $PPh_3$ and tri(o-tolyl)phosphine.

7. The process as claimed in claim 1, wherein transition metal catalyst in step (ii) further comprises co-catalyst selected from the group consisting of $Cu(OTf)_2$, $Cu(OAc)_2$, CuCl, CuBr, CuI $ZnCl_2$ and $Ag_2CO_3$.

8. The process as claimed in claim 2, wherein the deprotection of hydroxyl protecting group is carried out by a hydroxyl deprotecting agent comprising an inorganic base selected from potassium hydroxide, lithium hydroxide and sodium hydroxide, metal carbonates selected from potassium carbonate, sodium carbonate and cesium carbonate, metal alkoxides selected from sodium methoxide and sodium ethoxide; or an acid deprotecting agent selected from HCl, $H_2SO_4$, $HNO_3$, AcOH, HCOOH, $BF_3Et_2O$, $AlCl_3$ and $BBr_3$.

9. The process as claimed in claim 2, wherein the cyclization is carried out using an acid selected from the group consisting of HCl, $H_2SO_4$, $HNO_3$, AcOH, HCOOH, $BF_3Et_2O$, $AlCl_3$ and $BBr_3$.

10. The process as claimed in claim 1, further comprising the preparation of Tavaborole, which comprises the steps of:
(i) protecting primary hydroxyl moiety of a compound of 2a with acetic anhydride in presence of DCM and pyridine to obtain hydroxyl protected compound 3a;

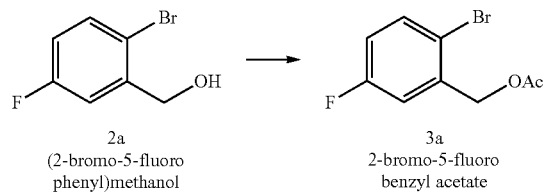 [SMILES: OCc1cc(F)ccc1Br ; CC(=O)OCc1cc(F)ccc1Br]

2a
(2-bromo-5-fluoro phenyl)methanol 3a
2-bromo-5-fluoro benzyl acetate (ii) converting the hydroxyl protected compound 3a obtained in step (i) into a borate compound 4a using bis(pinacolato)diboron via $PdCl_2(dppf)$ catalyzed cross-coupling reaction in presence of 1,4-dioxane and potassium acetate (KOAc), wherein the reaction is carried out at temperature between 70° C. to 120° C.;

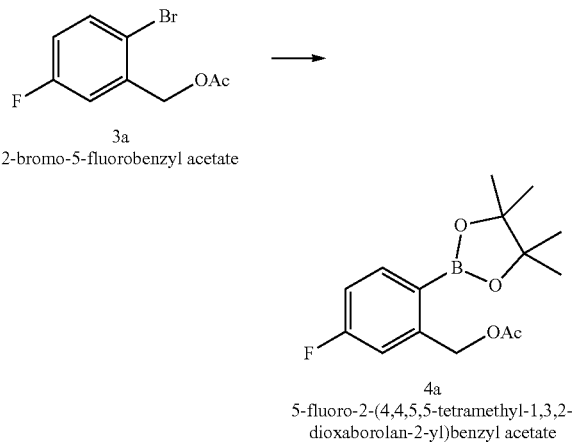

3a
2-bromo-5-fluorobenzyl acetate 4a
5-fluoro-2-(4,4,5,5-tetramethyl-1,3,2-dioxaborolan-2-yl)benzyl acetate (iii) simultaneous deprotection of hydroxyl protecting group and boronate ester group of borate compound 4a obtained in step (ii) by treatment with acid HCl or base NaOH to obtain Tavaborole.

11. The process as claimed in claim 1, further comprising the preparation of Tavaborole, which comprises the following steps:
(i) protecting primary hydroxyl moiety of a compound 2b with TBDMSCl in presence of dichloromethane (DCM) and imidazole to obtain hydroxyl protected compound 3b;

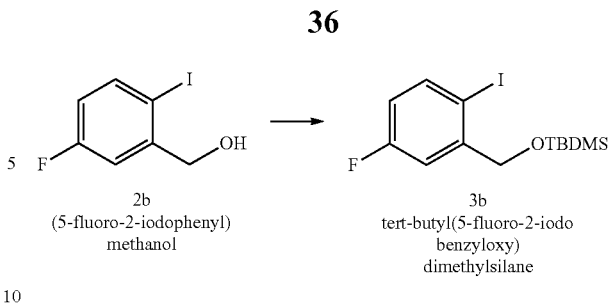

2b
(5-fluoro-2-iodophenyl) methanol 3b
tert-butyl(5-fluoro-2-iodo benzyloxy) dimethylsilane (ii) converting the hydroxyl protected compound 3b obtained in step (i) into a borate compound 4b using bis(pinacolato)diboron via $Pd(OAc)_2$ catalyzed cross-coupling reaction in presence of acetonitrile, Tri-O-tolylphosphine, $Cs_2CO_3$ and CuI;

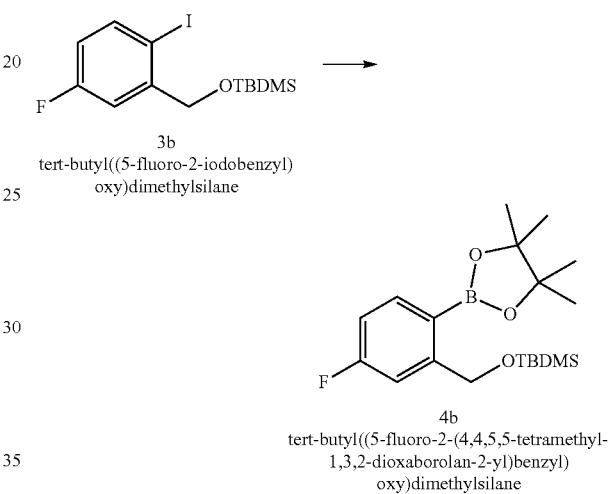

3b
tert-butyl((5-fluoro-2-iodobenzyl) oxy)dimethylsilane 4b
tert-butyl((5-fluoro-2-(4,4,5,5-tetramethyl-1,3,2-dioxaborolan-2-yl)benzyl) oxy)dimethylsilane (iii) treating compound 4b obtained in step (ii) with sodium periodate ($NaIO_4$) in presence of acetone, water and ammonium acetate followed by further treatment with HCl to obtain Tavaborole.

12. The process as claimed in claim 1, wherein the conversion of borate ester compound 4 into Tavaborole in step (ii) comprises the sub-steps of:
(i) oxidative cleaving of the borate ester compound of formula 4 into a compound of formula 6;

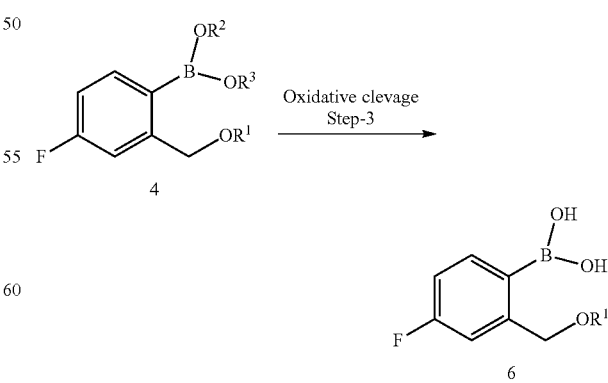

(ii) converting the compound of formula 6 into Tavaborole in presence of an acid;

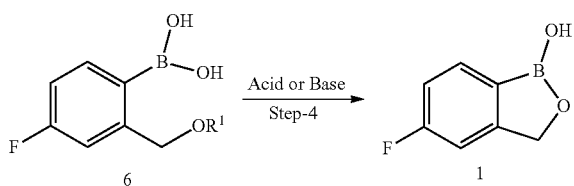

wherein

R¹ is hydrogen; and

R², R³ are members independently selected from H; substituted or unsubstituted $C_1$-$C_8$ alkyl; substituted or unsubstituted heteroalkyl $C_1$-$C_8$, substituted or unsubstituted aryl $C_5$-$C_{10}$; substituted or unsubstituted heteroaryl $C_5$-$C_{10}$; substituted or unsubstituted cycloalkyl $C_3$-$C_8$; substituted or unsubstituted heterocycloalkyl $C_3$-$C_8$; together with the atoms to which they are attached may be optionally joined to form a 4- to 8-membered ring.

13. The process as claimed in claim 12, wherein the oxidative cleaving in step (i) comprises treating the compound of formula 5 with $NaIO_4$ or $Pb(OAc)_4$ in presence of a solvent selected from the group consisting of $H_2O$, tetrahydrofuran, 1,4-dioxane, methanol and ethanol or mixtures thereof.

14. The process as claimed in claim 12, wherein the acid in step (ii) is selected from the group consisting of HCl, $H_2SO_4$, AcOH, HCOOH, $BF_3Et_2O$, $AlCl_3$ and $BBr_3$.

15. The process as claimed in claim 1, further comprises the purification of Tavaborole, wherein the purification comprises: (a) mixing Tavaborole in a solvent and treating the solution with an anti solvent;

(b) mixing Tavaborole in a solvent, optionally heating the solution to dissolve the compound and isolating the pure compound by cooling the solution;

(c) treating Tavaborole with silica gel in a solvent followed by recrystallization; and (d) dissolving Tavaborole in aqueous alkali solution followed by washing with Ethyl acetate, adjusting the pH of the aqueous layer to acidic with HCl, and filtering the precipitated solid;

wherein the solvent in any of the above process is selected from alkanes consisting of Hexanes, Toluene and cyclohexane, alcohols consisting of Methanol, Ethanol and Isopropyl alcohol, water, Acetonitrile, Tetrahydrofuran, Acetone, Ethyl acetate, and Dichloromethane or mixtures thereof; and wherein the anti-solvent is water.

* * * * *